(12) United States Patent
Babaris et al.

(10) Patent No.: US 12,171,417 B2
(45) Date of Patent: Dec. 24, 2024

(54) SURGICAL HANDPIECE HOUSING A VISIBLE LIGHT EMITTER AND ELEMENTS FOR TRANSMITTING THE VISIBLE LIGHT EMITTED BY THE VISIBLE LIGHT EMITTER

(71) Applicant: Stryker Corporation, Kalamazoo, MI (US)

(72) Inventors: Robin B. W. Babaris, Portage, MI (US); Keith Behnke, Freiburg (DE); Michael Laubenthal, Mattawan, MI (US); Adam J. Thelen, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 988 days.

(21) Appl. No.: 15/734,132

(22) PCT Filed: May 31, 2019

(86) PCT No.: PCT/US2019/034907
§ 371 (c)(1),
(2) Date: Dec. 1, 2020

(87) PCT Pub. No.: WO2019/232375
PCT Pub. Date: Dec. 5, 2019

(65) Prior Publication Data
US 2021/0212670 A1 Jul. 15, 2021

Related U.S. Application Data

(60) Provisional application No. 62/679,356, filed on Jun. 1, 2018.

(51) Int. Cl.
*A61B 17/00* (2006.01)
*A61B 90/92* (2016.01)
(Continued)

(52) U.S. Cl.
CPC .............. *A61B 17/00* (2013.01); *A61B 90/92* (2016.02); *A61B 2017/00115* (2013.01);
(Continued)

(58) Field of Classification Search
CPC .......... A61B 17/00; A61B 2017/00017; A61B 2017/00022; A61B 2017/00057;
(Continued)

(56) References Cited

U.S. PATENT DOCUMENTS 6,235,027 B1 5/2001 Herzon
6,607,384 B1 8/2003 Nakanishi
(Continued)

FOREIGN PATENT DOCUMENTS

CA 2456424 A1 2/2003
CN 105792766 A 7/2016
(Continued)

OTHER PUBLICATIONS

English language abstract for JP 2001-112779 A extracted from espacenet.com database on May 30, 2023, 1 page.
(Continued)

*Primary Examiner* — Ahmed M Farah
(74) *Attorney, Agent, or Firm* — Howard & Howard Attorneys PLLC

(57) ABSTRACT

A surgical handpiece and an autoclavable surgical handpiece are disclosed. The surgical handpiece and the autoclavable surgical handpiece include a housing and a visible light emitter disposed within the housing. The surgical handpiece includes a cable adjacent to the housing and a strain relief member coupled to the cable, the strain relief member being disposed adjacent to the housing and configured to transmit visible light emitted by the visible light emitter therethrough. The autoclavable surgical handpiece includes a potting material disposed between the visible light emitter (Continued)

and the housing, the potting material having a melting point above 120 degrees Celsius and being configured to thermally insulate the visible light emitter and to transmit visible light emitted by the visible light emitter therethrough.

13 Claims, 8 Drawing Sheets

(51) Int. Cl.
*A61B 90/00* (2016.01)
*A61B 90/30* (2016.01)
(52) U.S. Cl.
CPC ............... *A61B 2017/00221* (2013.01); *A61B 2017/00225* (2013.01); *A61B 2017/0042* (2013.01); *A61B 2017/00862* (2013.01); *A61B 2017/00907* (2013.01); *A61B 2090/306* (2016.02); *A61B 90/361* (2016.02)
(58) Field of Classification Search
CPC .. A61B 2017/00225; A61B 2017/0042; A61B 2017/00907; A61B 90/30; A61B 2090/304; A61B 2090/306; A61B 2090/308; A61B 2090/309; A61B 90/361; A61B 90/92; A61B 90/98; A61B 2017/00862
USPC ............................................................ 606/1
See application file for complete search history.

(56) References Cited

U.S. PATENT DOCUMENTS

| | | | |
|---|---|---|---|
| 8,545,502 | B2 | 10/2013 | Harp |
| 9,366,795 | B2 | 6/2016 | Weingaertner et al. |
| 9,463,287 | B1 | 10/2016 | Lorberbaum et al. |
| 9,848,857 | B2 | 12/2017 | Ware et al. |
| 10,537,472 | B2 | 1/2020 | Brennan et al. |
| 10,542,978 | B2 | 1/2020 | Chowaniec et al. |
| 10,820,912 | B2 | 11/2020 | Wildgen et al. |
| 2001/0029315 | A1 | 10/2001 | Sakurai et al. |
| 2006/0129140 | A1 | 6/2006 | Todd et al. |
| 2008/0312649 | A1 | 12/2008 | Guerra et al. |
| 2009/0173518 | A1 | 7/2009 | Flagler |
| 2011/0139851 | A1 | 6/2011 | McCuen |
| 2012/0316474 | A1* | 12/2012 | Bonutti ................. A61B 90/06 601/2 |
| 2014/0113243 | A1* | 4/2014 | Boutoussov ........... A61C 1/081 433/29 |
| 2014/0210116 | A1* | 7/2014 | Schaller ............ B29C 45/14622 264/1.1 |
| 2015/0182230 | A1* | 7/2015 | Belagali ..................... B25F 5/02 606/82 |
| 2015/0327919 | A1* | 11/2015 | Clopp ................. A61B 17/3205 606/41 |
| 2016/0256184 | A1 | 9/2016 | Shelton, IV et al. |
| 2017/0135859 | A1* | 5/2017 | Scheller ............. A61F 9/00821 |
| 2017/0172583 | A1 | 6/2017 | Wildgen et al. |
| 2017/0209145 | A1 | 7/2017 | Swayze et al. |
| 2017/0249431 | A1 | 8/2017 | Shelton, IV et al. |
| 2018/0110502 | A1 | 4/2018 | Ware et al. |
| 2019/0343537 | A1 | 11/2019 | Fennessy et al. |

FOREIGN PATENT DOCUMENTS

| | | | | |
|---|---|---|---|---|
| CN | 105792783 | A | 7/2016 | |
| CN | 107708777 | A | 2/2018 | |
| DE | 202006020084 | U1 * | 10/2007 | ............. A61B 18/22 |
| EP | 2218409 | A1 | 8/2010 | |
| JP | 2001112779 | A | 4/2001 | |
| JP | 2004158198 | A | 6/2004 | |
| JP | 2006500998 | A | 1/2006 | |
| JP | 2014223310 | A | 12/2014 | |
| WO | 2018201027 | A1 | 11/2018 | |

OTHER PUBLICATIONS

English language abstract and machine-assisted English translation for JP 2004-158198 A extracted from espacenet.com database on May 30, 2023, 8 pages.
English language abstract for JP 2006-500998 A extracted from espacenet.com database on May 30, 2023, 1 page.
English language abstract for JP 2014-223310 A extracted from espacenet.com database on May 30, 2023, 2 pages.
Partial International Search Report for Application No. PCT/US2019/034907 dated Dec. 20, 2019, 4 pages.
International Search Report for Application No. PCT/US2019/034907 dated May 14, 2020, 4 pages.
English language abstract for CN 105792766 A extracted from espacenet.com database on Aug. 13, 2024, 3 pages.
English language abstract for CN 105792783 A extracted from espacenet.com database on Aug. 13, 2024, 2 pages.
English language abstract for CN 107708777 A extracted from espacenet.com database on Aug. 13, 2024, 2 pages.

\* cited by examiner

SURGICAL HANDPIECE HOUSING A VISIBLE LIGHT EMITTER AND ELEMENTS FOR TRANSMITTING THE VISIBLE LIGHT EMITTED BY THE VISIBLE LIGHT EMITTER

CROSS-REFERENCE TO RELATED APPLICATIONS

The subject patent application is a national stage of International Patent Application No. PCT/US2019/034907, filed on 31 May 2019, which claims priority to and all the benefits of U.S. Provisional Patent Application Ser. No. 62/679,356, which was filed on 1 Jun. 2018, the disclosures of which are hereby incorporated by reference in their entirety.

BACKGROUND

Surgical procedures typically require a surgeon to use a variety of surgical devices. For example, a surgical procedure may require a surgeon to use drills, saws, aspirators, electrodes, probes, imaging devices, etc. To satisfy this need, surgical systems often provide surgeons the ability to use a plurality of surgical devices. However, as surgical procedures and surgical systems grow in complexity, surgeons are required to use more surgical devices and more complex surgical devices during surgical procedures. Furthermore, some surgical procedures require multiple surgeons, each of which operating a plurality of surgical devices.

As such, there remains a need in the art for a surgical system to more quickly present information concerning the surgical devices to a surgeon and for a surgical system to better identify the surgical devices being used in a surgical procedure.

Also, there remains a need to have indicators on autoclavable instruments.

SUMMARY OF THE DISCLOSURE

One instance of a surgical system is provided. The surgical system comprises a surgical handpiece comprising a visible light emitter, a controller configured to determine a state of the surgical handpiece and to control the visible light emitter to emit visible light based on the state of the surgical handpiece, a light sensor configured to produce an output signal based on sensing the visible light, and a second surgical system configured to determine an identity of the surgical handpiece based on the output signal.

One instance of a method of operating a surgical system comprising a surgical handpiece, which comprises a visible light emitter, is provided. The method comprises steps of determining a state of the surgical handpiece, controlling the visible light emitter to emit visible light based on the state of the surgical handpiece, producing an output signal based on sensing the visible light emitted by the visible light emitter, and determining an identity of the surgical handpiece based on the output signal.

One instance of a surgical handpiece is provided. The surgical handpiece comprises a housing having a first end and a second end and a cable adjacent to the housing. The surgical handpiece also comprises a visible light emitter disposed within the housing and a strain relief member coupled to an external surface of the cable and disposed adjacent the first end of the housing, the strain relief member being configured to transmit visible light emitted by the visible light emitter therethrough.

One instance of an autoclavable surgical handpiece is provided. The autoclavable surgical handpiece comprises a housing having a first end and a second end, a visible light emitter disposed within the housing, and a potting material disposed between the visible light emitter and the first end of the housing. The potting material has a melting point above 120 degrees Celsius and is configured to thermally insulate the visible light emitter and to transmit visible light emitted by the visible light emitter therethrough.

BRIEF DESCRIPTION OF THE DRAWINGS

Referring now to the drawings, exemplary illustrations are shown in detail. Although the drawings represent examples, the drawings are not necessarily to scale and certain features may be exaggerated or schematic in form to better illustrate and explain a particular aspect of an illustrative example. Any one or more of these aspects can be used alone or in combination within one another. Further, the exemplary illustrations described herein are not intended to be exhaustive or otherwise limiting or restricting to the precise form and configuration shown in the drawings and disclosed in the following detailed description. Exemplary illustrations are described in detail by referring to the drawings as follows.

DETAILED DESCRIPTION

Figure 1:
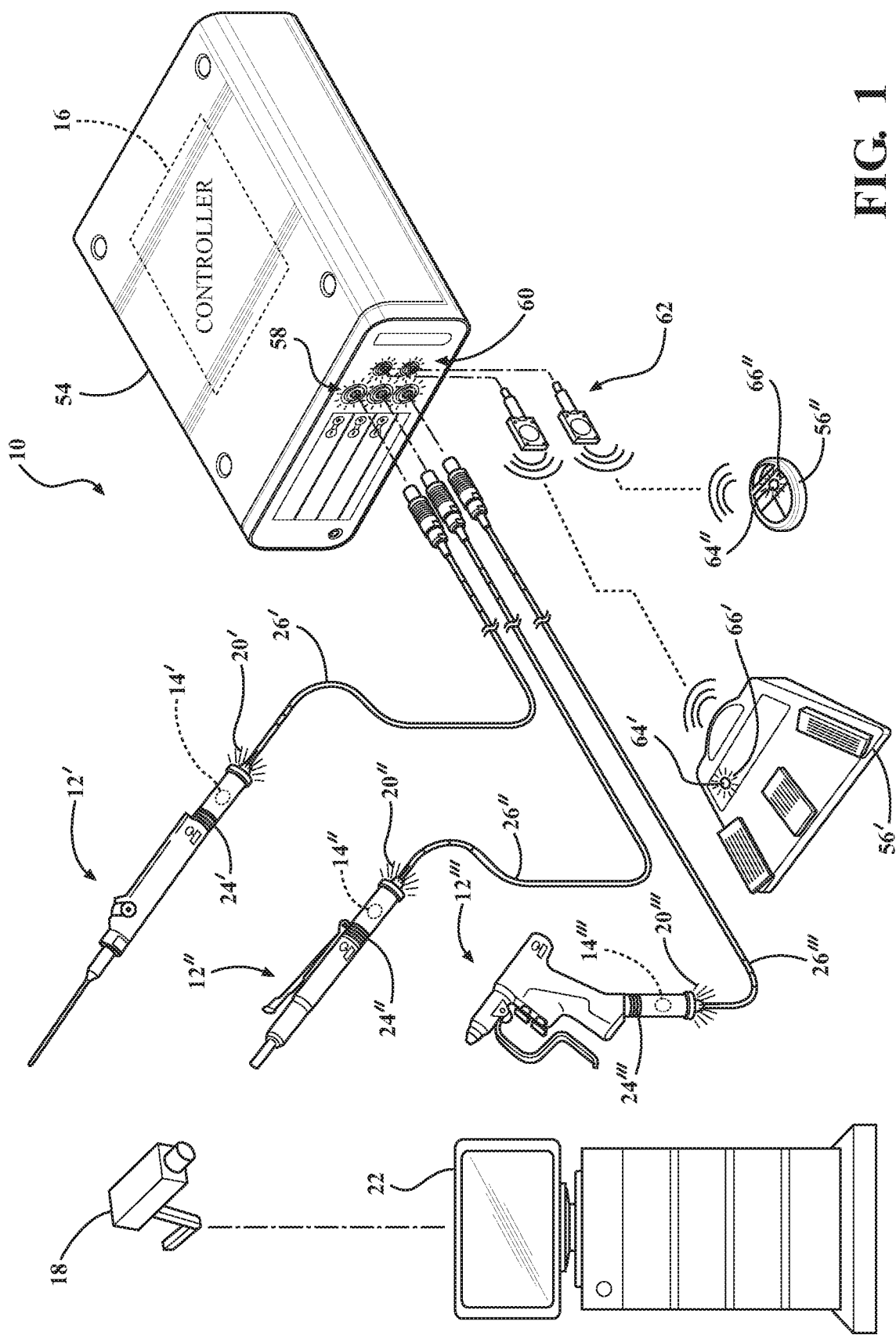
FIG. 1 is an exploded view of an instance of a surgical system comprising a plurality of surgical handpieces, a controller, a plurality of control devices, a light sensor, and a surgical workflow system.

Referring to FIG. 1, one instance of a surgical system 10 is shown. As shown, the surgical system 10 includes a surgical handpiece 12 which includes a light emitter 14, which is configured to emit the visible light 20. In the instance of FIG. 1, the surgical handpiece 12 is illustrated as surgical handpieces 12', 12", 12''' and the light emitters 14 are illustrated as light emitters 14', 14", 14'''. Additionally, the visible light 20 emitted by the light emitters 14', 14", 14''' is illustrated as visible light 20', 20", 20''', respectively.

Herein, components of the surgical system 10 may be referred to generically or specifically. For example, the terms, "surgical handpiece 12" and "surgical handpieces 12''', may be interpreted as a generic categorization of surgical handpieces, of which the surgical handpieces 12', 12'', 12''' are examples thereof. In contrast, the terms, "surgical handpiece 12'", "surgical handpiece 12''", "surgical handpiece 12'''", and "surgical handpieces 12', 12'', 12'''" refer to the specific surgical handpieces 12', 12'', 12''' shown in FIG. 1. Similarly, other components of the surgical system 10, such as light emitters 14 and the visible light 20 emitted by the light emitters 14, may also be referred to generically or specifically.

The surgical system 10 also includes a controller 16, which is configured to determine a state of the surgical handpiece 12 and to control the light emitter 14 to emit visible light 20 based on the state of the surgical handpiece 12. Additionally, the surgical system 10 includes a light sensor 18, which is configured to produce an output signal based on sensing the visible light 20, and a second surgical system 22, which is configured to determine an identity of the surgical handpiece 12 based on the output signal received from the light sensor 18. In FIG. 1, the second surgical system 22 is illustrated as a surgical workflow system.

The surgical system 10 may include any suitable number of surgical handpieces 12. For example, the surgical system 10 may include the three surgical handpieces 12', 12'', 12''', as shown in FIG. 1. However, in other instances, the surgical system 10 may include one, two, four, or any other number of surgical handpieces 12. It should be noted that, herein, the surgical handpieces 12 may be referred to in a plural or a singular form, such references being non-limiting.

The surgical handpieces 12 may be a variety of different types of surgical handpieces. For example, each surgical handpiece 12 may be any of the surgical handpieces 12 shown in FIG. 1. In other instances of the surgical system 10, the surgical handpiece 12 may be a surgical handpiece not represented by the surgical handpieces 12', 12'', 12'''. For example, the surgical handpieces 12 may be a variety of surgical handpieces which, when operated, perform one or more predetermined functions in the treatment or care of a patient. For instance, one or more of the surgical handpieces 12 may include a specialty drill, a high-powered tapered drill, a modular handpiece, a high-speed pencil-grip drill, a pneumatic drill, a drill for intraoperative procedures, a drill for oral surgery, a drill for ENT surgery, a sagittal, oscillating or reciprocating saw, a microdebrider, an ultrasonic aspirator, electrodes, probes, or any hand-held imaging device, such as an endoscope or camera, and the like.

Electrosurgical devices, ultrasound devices, and other surgical handpieces 12 may also be employed as example surgical handpieces. Electrosurgical instruments may be of any suitable type, including those that use diathermy with either unipolar or bipolar current (commonly referred to simply as unipolar devices and bipolar devices), and advanced devices such as harmonic scissors and argon beam and laser devices. As another example, surgical handpieces 12 that are not handheld, such as surgical robots, lighting systems, and cameras, may also be employed.

Figure 5A:
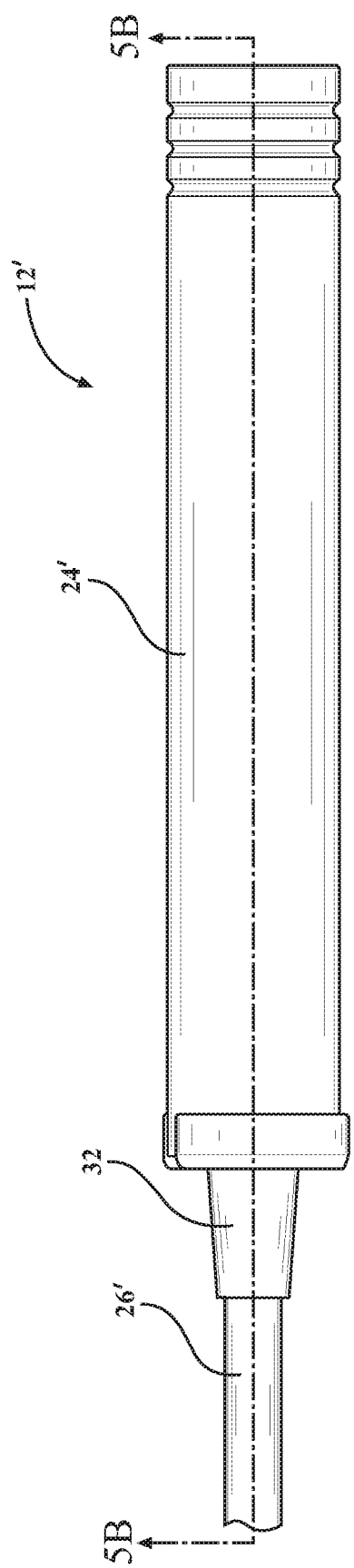
FIG. 5A is a perspective of a housing of a surgical handpiece.

Referring to FIG. 5A, a perspective view of a surgical handpiece 12 is shown to further illustrate a structure of the surgical handpieces 12. Referring back to FIG. 1, the surgical handpieces 12 each include a housing 24. For example, the surgical handpieces 12', 12'', 12''' include the housings 24', 24'', 24'''. In FIG. 5A, the housing 24' of surgical handpiece 12' is shown. Specifically, in FIG. 5A, the housing 24' of the surgical handpiece 12' of FIG. 1 is shown to illustrate an example instance of the surgical handpieces 12 and to further illustrate the structure of the surgical handpieces 12. Therefore, any description herein of the surgical handpiece 12' or any components thereof may be applied to all surgical handpieces 12 and to respective components thereof. Additionally, any description herein of components coupled to the surgical handpiece 12', such as cable 26' (shown in FIGS. 5A-5C), may be applied to all such components, such as cables 26 (shown in FIG. 1).

Figure 5B:
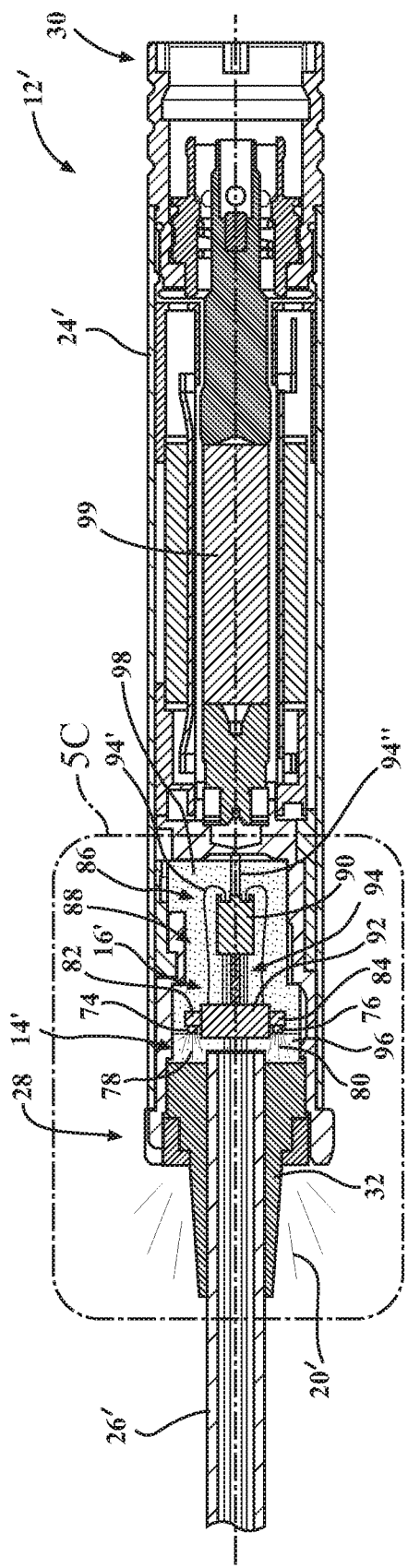
FIG. 5B is a partial cross-sectional view of the housing of the surgical handpiece of FIG. 5A.

FIG. 5B is a cross-sectional view of the housing 24' of the surgical handpiece 12' in FIG. 5A. As shown in FIG. 5B, the housing 24' of the surgical handpiece 12' has a first end 28 and a second end 30. The surgical handpiece also includes a cable 26' adjacent to the housing 24', a light emitter 14' disposed within the housing 24', and a strain relief member 32 coupled to an external surface of the cable 26' and disposed adjacent the first end 28 of the housing 24' In some instances, the strain relief member 32 seals the cable 26' to the housing 24'. Additionally, the strain relief member has a melting point above 120 degrees Celsius and is configured to transmit visible light 20' emitted by the light emitter 14' therethrough.

Figure 5C:
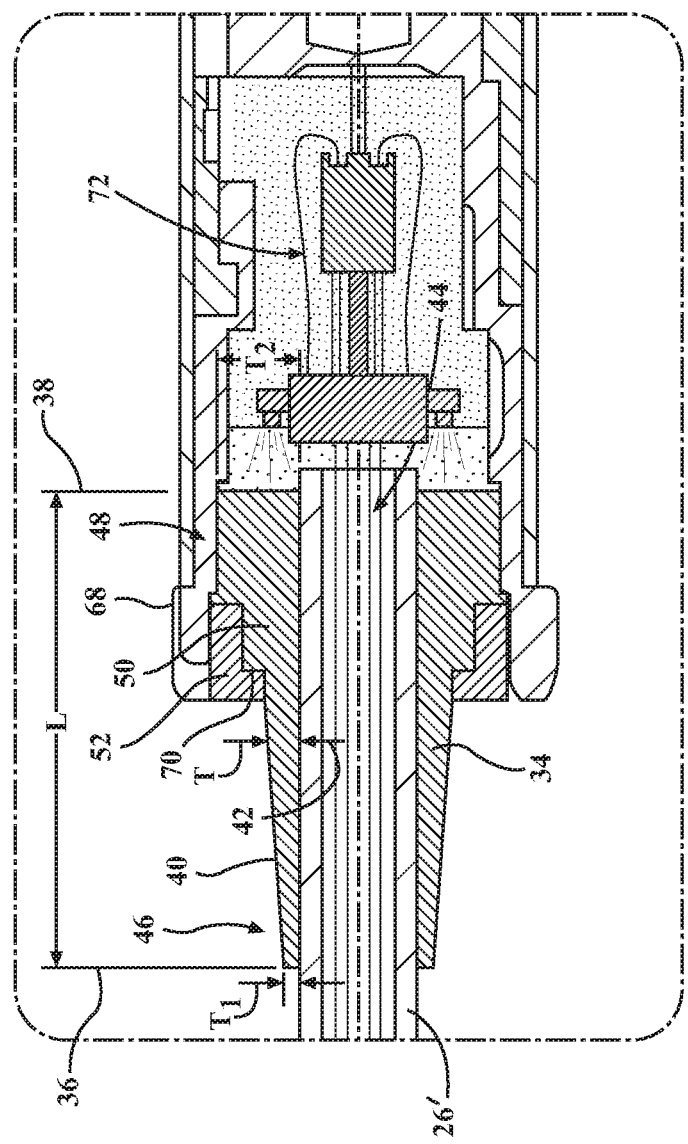
FIG. 5C is a magnified view of the partial cross-sectional view of the housing of the surgical handpiece of FIG. 5B.

FIG. 5C illustrates a magnified view of the partial cross-sectional view in FIG. 5B, with a focus on the strain relief member 32. As shown, the strain relief member 32 includes a body 34, the body 34 having a first end 36 and a second end 38 defining a length L and an external surface 40 and an internal surface 42 defining a lumen 44 extending along the length L, which may be configured to receive the cable 26'. Additionally the external surface 40 and the internal surface 42 define a thickness T therebetween. Also shown in FIG. 5C, the strain relief member 32 includes a first region 46 having a first thickness $T_1$ and a second region 48 having a second thickness $T_2$, the second thickness $T_2$ being greater than the first thickness $T_1$.

In FIG. 5C, the strain relief member 32 includes a flange 50 and the housing 24' of the surgical handpiece 12' includes a shelf 52. In such an instance, the strain relief member 32 is disposed adjacent to the first end 28 of the housing 24' by being coupled to the first end 28 of the housing 24'. As shown, the flange 50 of the strain relief member 32 separates the first and second region 46, 48 of the strain relief member 32. Also shown, the housing 24' of the surgical handpiece 12' includes an external surface 68 and an internal surface 70, the internal surface 70 comprising the flange 52 of the housing 24'. Furthermore, the internal surface 70 of the housing 24' defines a second lumen 72, wherein the flange 50 of the strain relief member 32 and the flange 50 of the housing 24' are configured to abut, coupling the strain relief member 32 to the housing 24'. As such, the flange 50 of the strain relief member 32 engages the shelf 52 of the surgical handpiece 12', allowing the strain relief member 32 to be coupled to the first end 28 of the housing 24' and for the flange 50 and the second region 48 of the surgical handpiece 12' to be disposed within the housing 24'. In some instances, because the strain relief member 32 is coupled to an external surface of the cable 26', by coupling the strain relief member 32 to the first end 28 of the housing 24', the strain relief member 32 seals the cable 26' to the housing 24'. Such a seal is advantageous in instances where the surgical handpieces 12 are autoclaved.

It should be noted that the strain relief member 32 may be disposed adjacent to the first end 28 of the housing 24' using other means. For example, in some instances, the strain relief member 32 may omit the flange 50 and the housing 24' may omit the shelf 52. In such instances, the strain relief member 32 may be molded directly into the housing 24' or the strain relief member 32 may be coupled to the housing 24' using an adhesive. Furthermore, it should be noted that the strain relief member 32 may be coupled to the housing 24' using a combination of the above-stated means. For example, in one such instance, the flange 50 of the strain relief member 32 may be created a by-product of molding the strain relief member 32 directly into the housing 24' including the shelf 52. In another example, the flange 50 of the strain relief member 32 may be coupled to the shelf 52 of the strain relief member using an adhesive.

The housing 24' and the strain relief member 32 may be of any suitable shape and size. For example, in various instances, the shape and the size of the housing 24' of the surgical handpiece 12' may be altered for ergonomic purposes. As such, in instances where the strain relief member 32 is molded directly into the housing 24', the shape and size of the strain relief member 32 may also be altered. As another example, the housing 24' and/or the strain relief member 32 may have a different shape and size depending on the size of the cable 26'. As yet another example, the strain relief member 32 may have a longer or shorter length L. In an instance where the cable 26' extends further into the second lumen 72, it may be advantageous for the strain relief member 32 to have a longer length L and to also extend further into the second lumen 72. Similarly, in an instance where a length of the cable 26' outside the housing 24' is maximized and the cable 26' does not extend as far into the housing 24' as shown in FIG. 5C, the strain relief member 32 may accordingly have a shorter length L.

Additionally, the strain relief member 32 may be formed of various materials. For example, the strain relief member 32 may be formed of a material with a high visible light transmittance (such as a material with a visible light transmittance of greater than 50%) to allow the strain relief member 32 to more easily transmit the visible light 20' emitted by the light emitter 14' therethrough. For example, the strain relief member 32 may be formed of a transparent epoxy resin or silicone. In another example, the strain relief member 32 may be formed of a material with a color which may be different than the color of the external surface of the cable 26', allowing the visible light 20' transmitted therethrough to be more discernable. In such an instance, the cable 26' may be a black cable and the strain relief member 32 may be formed of a material that is white and semi-transparent. In yet another example, the strain relief member 32 may be formed of an elastomeric material, allowing the strain relief member 32 to bend with the cable 26', which the strain relief member 32 is coupled to. For instance, the strain relief member 32 may comprise silicone, epoxy, or any other flexible material. In still another example, the strain relief member 32 may be formed of a material which creates a seal between the housing 24' and the strain relief member 32. For instance, the strain relief member 32 may be molded of a plastic or a rubber directly into the housing 24', creating a seal between the housing 24' and the strain relief member 32, allowing the surgical handpiece 12' to be sterilized in high-pressure and/or high-temperature cleaning devices, such as autoclaves. The strain relief member 32 may have a melting point above 120 degrees Celsius to allow the surgical handpiece 12' to be sterilized in such an autoclave. In still yet another example, the strain relief member 32 may be formed as a single member or as two or more separate members. For instance, the strain relief member 32 may be molded as a single member directly into the housing 24' or as two separate members before being disposed adjacent to the housing 24'.

The surgical handpiece 12' may also include a potting material 86 disposed between the visible light emitter 14' and the first end 28 of the housing 24'. The potting material 86 is configured to thermally insulate the visible light emitter 14' and to transmit visible light emitted by the visible light emitter therethrough. The potting material may serve to hermetically seal the surgical handpiece 12' and prevent steam from entering the handpiece and damaging internal components sensitive to moisture and/or high temperature. Such internal components may include the wires 94, the wire distribution system 88 that includes the wire distributor 90 and the flexible printed circuit board 92, the controller 16', and the visible light emitter 14', all of which will be described in further detail herein. Other internal components, such as sensors of the handpiece 12' may also be encased in the potting material 86. As such, the potting material 86 may be formed of any suitable material. For example, the potting material 86 may have a melting point above 120 degrees Celsius to allow the surgical handpiece 12' to be sterilized in an autoclave and to thermally insulate the internal components when the surgical handpiece 12' is being sterilized in an autoclave.

The potting material 86 may be formed of a material with a high visible light transmittance (such as a material with a visible light transmittance of greater than 50%) to allow the potting material 86 to more easily transmit the visible light 20' emitted by the light emitter 14' therethrough. For example, the potting material 86 may be formed of a transparent epoxy resin or silicone.

The potting material 86 may be formed as a single member or as two or more separate portions 96, 98. For instance, the potting material 86 may be molded as a single member directly into the housing 24' or as two separate portions 96, 98 before being disposed within the housing 24'. In FIG. 5B, the two separate portions 96, 98 are a portion 96 between the visible light emitter 14' and the strain relief member 32 and a portion 98 between the visible light emitter 14' and the second end 30 of the handpiece 24'. Each of these portions 96, 98 may have the same or different compositions. For example, the portions 96, 98 may have a different visible light transmittance. The portion 96 between the strain relief member 32 and the visible light emitter 14' could be transparent, and the portion between the visible light emitter 14' and the second end 30 of the handpiece 24' could be opaque.

The potting material 86 may also be formed of a same material as the strain relief member 32. For example, both the strain relief member 32 and the potting material 86 may be formed of a transparent epoxy resin. In a further instance, the strain relief member 32 and the potting material 86 may be integral to one another. In such an instance, the strain relief member 32 and the potting material 86 may be molded as a single member directly into the housing 24'.

The surgical handpiece 12' may include any suitable number of light emitters 14. For example, as shown in FIG. 5B, the light emitter 14' of the surgical handpiece 12' includes two light emitters 74, 76. As shown, light emitters 74, 76 are disposed within the first end 28 of the housing 24'. In such an instance, the strain relief member 32 is further configured to transmit at least one of visible light 78, 80 emitted by the light emitters 74, 76, respectively, therethrough as the visible light 20'. For instance, in some instances, the visible light 78 emitted by light emitter 74 and the visible light 80 emitted by light emitter 76 may be different. In one such instance, the visible light 78, 80 may be of a different color. As such, the strain relief member 32 may be configured to transmit just one of the visible light 78, 80 or both the visible light 78, 80 sequentially or simultaneously as visible light 20'. For purposes of clarity, the light emitters 74, 76 may be referred to in combination herein as "the light emitters 14'". Furthermore, the light emitters 14' may be disposed in a variety of locations within the housing 24'. For instance, the light emitters 14' may be disposed within the second lumen 72, such as on a portion of the internal surface 70 of the housing 24' which extends into the second lumen 72. In the instances of FIGS. 5B and 5C, the light emitters 14' are disposed such that the light emitted 78, 80 by the light emitters 74, 76 are directed towards the strain relief member 32. In this way, an amount of the visible light 20' transmitted through the strain relief member 32 may be increased. Additionally, the internal surface 70 of the housing 24' may include a reflective material to aid in transmitting the visible light 78, 80 through the strain relief member 32. The first end 28 may also include a reflective material to aid in transmitting the visible light 20' for better visibility of the visible light 20' by an operator of the surgical system 10.

Furthermore, the light emitters 14' may be any suitable light emitter. For example, the light emitters 14' may be at least one RGB LED configured to emit visible light with a light color of red, green, blue, or combinations thereof. In other instances, the light emitters 14' may be any other type of light emitter capable of emitting visible light, such as a fiber optic medium, a miniature LED, a bi-color LED, or a tri-color LED.

Referring back to FIG. 1, the surgical system 10 includes the controller 16 which are configured to determine the state of the surgical handpiece 12 and to control the light emitter 14 to emit the visible light 20 based on the state of the surgical handpiece 12. In some instances, the controller 16 may be disposed within the housing 24' of the surgical handpiece 12' and may be configured to control the light emitters 14' of the surgical handpiece 12'. In such an instance, the controller 16 may be coupled to the light emitters 14' within the housing 24'. For example, as shown in FIG. 5B, the controller 16' of the surgical handpiece 12' includes controllers 82 and 84. The controllers 82 and 84 are coupled to the visible light emitters 74 and 76, respectively within the housing 24'.

As shown in FIG. 5B, the surgical handpiece 12' may include a wire distribution system 88 configured to distribute wires 94 within the cable 26' to various components of the surgical handpiece 12'. The wire distribution system 88 includes wire distributor 90 and a flexible printed circuit board 92. As shown in FIG. 5B, the wire distributor 90 routes the wires 94 to the flexible printed circuit board 92 to be coupled to the controllers 16'. The wire distributor 90 also routes the wires 94 to other components of the surgical handpiece 12'. For example, in FIG. 5B, wires 94' of the wires 94 are routed to the flexible printed circuit board 92 to be coupled to the controllers 82, 84 by the wire distributor 90. In an example instance, the controllers 82, 84 may receive power and/or data from the surgical console 54 via the wires 94' to determine the state of the surgical handpiece 12'. Also shown in FIG. 5B, wires 94" of the wires 94 are routed toward the second end region 30 of the surgical handpiece 12'. In such an instance, the wires 94" may be coupled to a variety of other components of the surgical handpiece 12', such as a second controller of the surgical handpiece 12', a sensor, and/or a motor 99.

In FIG. 5B, the wire distributor 90 and the flexible printed circuit board 92 are cylindrical such that that the wires 92 may be passed through the flexible printed circuit board 92 and the wire distributor 90 before being the distributed by the wire distributor 90. In other instances, the wire distributor 90 and the flexible printed circuit board 92 may include any other suitable shape such that the wires 94 may be passed around or through the flexible printed circuit board 92 before being distributed by the wire distributor 90.

In other instances, the wires 94 of the cable 26' may be distributed using other means. For example, the surgical handpiece 12' may omit the wire distribution system 88. The wire distribution system 88 may also omit the wire distributor 90 and/or the flexible printed circuit board 92. For instance, the flexible printed circuit board 92 and the wire distributor 90 may be integral to one another such that the wire distributor 90 directly connects the wires 94' to the controller 16' and distributes the wires 94" to other components of the surgical handpiece 12'. The wire distribution system 88 may also include other components suitable for distributing the wires 94 to components of the surgical handpiece 12'. It is also contemplated that the wire distributor 90 and the flexible printed circuit board 92 may be arranged in variety of other means. For instance, the wires 94 may pass through and be distributed by the wire distributor 90 before passing through the flexible printed circuit board 92.

Furthermore, the controller 16 may include a processor and a memory to aid in determining the state of the surgical handpiece 12 and controlling the light emitter 14. The processor may be any processor suitable for processing data. Similarly, the memory may be any memory suitable for storage of data and computer-readable instructions. For example, the memory may be a local memory, an external memory, or a cloud-based memory embodied as random access memory (RAM), non-volatile RAM (NVRAM), flash memory, or any other suitable form of memory.

Figure 2A:
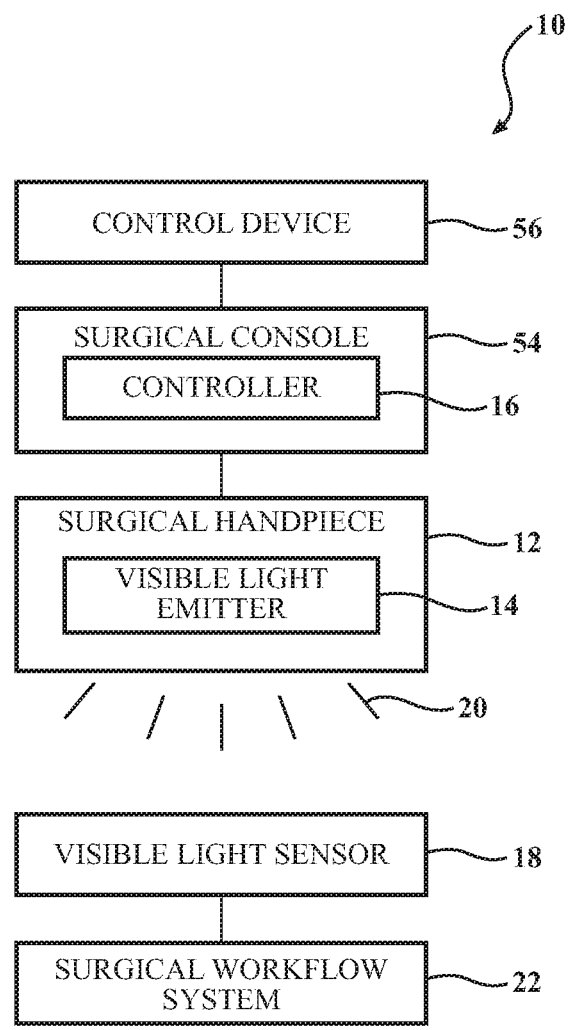
FIG. 2A is a schematic view of an instance of the surgical system wherein a surgical console comprises the controller of the surgical system.
Figure 2B:
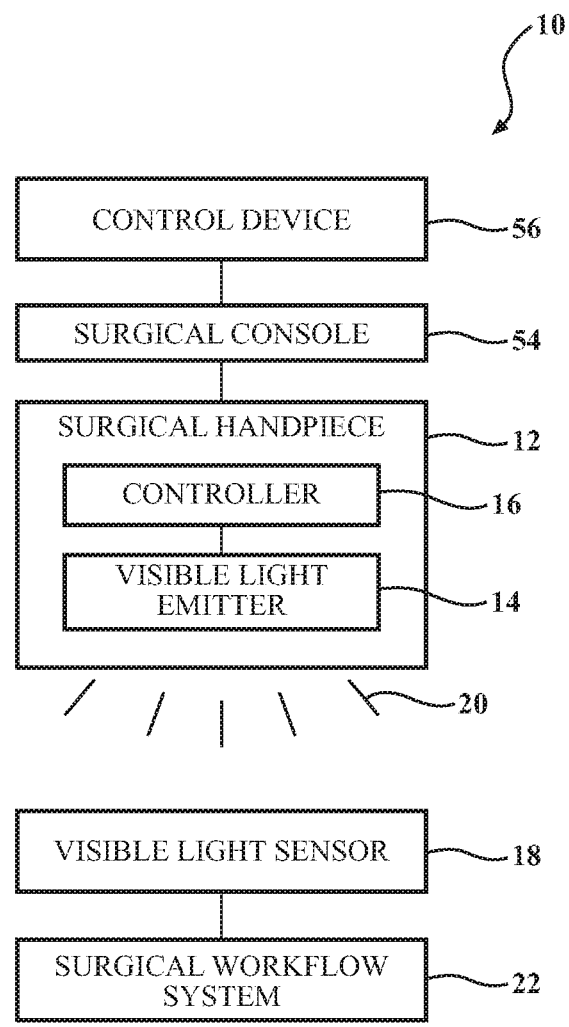
FIG. 2B is a schematic view of an instance of the surgical system wherein a surgical handpiece comprises the controller of the surgical system.

Additionally, a variety of components of the surgical system 10 may include the controller 16. For example, FIGS. 2A and 2B illustrate schematic views of two example instances of the surgical system 10, wherein different components of the surgical system 10 include the controller 16. In the instance of FIG. 2A (and the instance of FIG. 1), the surgical console 54 includes the controller 16. As such, the surgical console 54 controls the light emitter 14. In the instance of FIG. 2B, the surgical handpiece 12 includes the controller 16. As such, the surgical handpiece 12 controls the light emitter 14. Herein, the instance of FIG. 2A will be referred to as the "surgical console controller example" and the instance of FIG. 2B will be referred to as the "surgical handpiece controller example". It should be appreciate that features of the surgical handpiece controller example can be used with the surgical console controller example, and vice-versa.

It should be noted that, while in some instances the controller 16 is not located in the surgical console 54 or in the surgical handpiece 12, the surgical console 54 or the surgical handpiece 12 may still include a controller. For example, in the "surgical console controller example", the surgical handpiece 12 may include its own controller for operating the surgical handpiece 12, while the surgical console 54 includes the controller 16 configured to control the light emitters 14. Similarly, in the "surgical handpiece controller example", the surgical console 54 may include its own controller for operating the surgical console 54, while the surgical handpiece 12 includes the controller 16 configured to control the light emitters 14.

In some instances, at least a part of the controller 16 may be located in both the surgical console 54 and in the surgical handpiece 12. In such an instance, some operations of the controller 16 may be executed by the part of the controller 16 located in the surgical console 54 and some operations may be executed by the part of the controller 16 located in the surgical handpiece 12. In a specific instance, the part of the controller 16 located in the surgical handpiece 12 may be coupled to the part of the controller 16 located in the surgical console 54 via a CAN communication network (not shown in FIGS. 5A-5C), allowing the parts of the controller 16 located in the surgical handpiece 12 and the surgical console 54 to communicate in a quick and efficient manner.

Furthermore, it should be noted that, while the controller 16 is located in the surgical console 54 or the surgical handpiece 12 in FIGS. 1, 2A, and 2B, in other instances, other components of the surgical system 10 may include the controller 16. For example, the controller 16 may be located in the control devices 56. Furthermore, the controller 16 may be separate from any component of the surgical system 10 or may be located in a separate computing device, such as a desktop computer, a cellular phone, a smart phone, a laptop, a tablet, or a wearable mobile device.

The light sensor 18 may be any device suitable for sensing the visible light 20. For example, in the instance shown in FIG. 1, the light sensor 18 is illustrated as a camera. However, in other instances, the light sensor 18 may be a device including a photodiode, a digital camera, a webcam, a video camera, a livestream broadcast camera, or combinations thereof. Accordingly, the output signal produced by the light sensor 18 may vary based on the light sensor 18. For example, if the light sensor 18 is a digital camera, the output signal image data may be a photo. In another example, if the light sensor 18 is a video camera, the output signal may be a video. In yet another example, if the light sensor 18 is a device including a photodiode, the output signal may be a digital signal.

Furthermore, the light sensor 18 may be located in any location suitable for sensing the visible light 20. For example, the light sensor 18 may be coupled to a wall or an operating table of an operating room including the surgical system 10. In another example, the light sensor 18 may be coupled to a component of the surgical system 10, such as a tracking camera, etc. For example, in an instance where the second surgical system 22 is a desktop computer including a display, the light sensor 18 may be mounted to the display of the second surgical system 22. In yet another example, the light sensor 18 may be located on an operator of the surgical system 10. For instance, the light sensor 18 may be coupled to a body of a surgeon operating the surgical system 10.

The second surgical system 22 may be any system suitable for determining the identity of the surgical handpiece 12 based on the output signal from the light sensor 18. For example, the second surgical system 22 may be any suitable computing system. In the instance of FIG. 1, the second surgical system 22 includes a desktop computer, which includes a processor and a memory for determining the identity of the surgical handpiece 12 based on the output signal from the light sensor 18. Similarly, in other instances, the second surgical system 22 may include a cellular phone, a smart phone, a laptop, a tablet, a wearable mobile device, or any other device suitable for determining the identity of the surgical handpiece 12.

In some instances, the second surgical system 22 may be further configured to perform a variety of tasks based on the identity of the surgical handpiece 12. For example, in FIG. 1, the second surgical system 22 is a surgical workflow system for use in an operating room during a surgical procedure. As such, the second surgical system 22 may be configured to determine, based on the identity of the surgical handpiece 12, a step (current, previous, or subsequent) of the surgical procedure, instructions for the step of the surgical procedure, whether the surgical handpiece 12 is acceptable for the step of the surgical procedure, warnings for the step of the surgical procedure, whether the surgical procedure requires additional surgical handpieces 12 or auxiliary equipment (operating room lighting, video and sound recording devices, suction devices, imaging devices, etc.), and/or whether the surgical handpiece 12 includes an attachment. The second surgical system 22 may then proceed with further steps to assist an operator of the surgical system 10. For instance, after determining the identity of the surgical handpiece 12, the second surgical system 22 may display a GUI on a screen in the operating room, the GUI providing a step of the surgical procedure, instructions, and/or warnings regarding the identified surgical handpiece 12. In a specific instance where the surgical handpiece 12 is a drill and the second surgical system 22 includes a head-mounted display device, the head-mounted display device may overlay a desired entry angle for the drill on a patient's body.

It should be appreciated that the second surgical system 22 may include multiple components, which may be located at any suitable location. For example, in the instance of FIG. 1, the second surgical system 22 is a surgical workflow system including a computing system and a display, both of which are located in an operating room including the surgical system 10. However, in other instances, the second surgical system 22 may include a computing system and a display, the display being located in the operating room and the computing system being located in a room within a vicinity of the operating room or in a location remote to the operating room. For example, the computing system of the second surgical system 22 may be located in a remote location and may receive the output signal from the light sensor 18 via a server, determine the identity of the surgical handpiece 12 at the remote location, and provide a step of the surgical procedure, instructions, and/or warnings regarding the identified surgical handpiece 12 to the display of the second surgical system 22 located in the operating room, via a server. The display may then display the step of the surgical procedure, the instructions, and/or the warnings to an operator of the surgical system 22 in the operating room.

In the instance of FIG. 1, the surgical system 10 includes a surgical console 54, which is configured to send a drive signal to the surgical handpiece 12. The surgical system 10 also includes a control device 56, which is in communication with the surgical handpiece 12 and the surgical console 54 such that the control device 56 is configured to control the surgical handpiece 12 via the surgical console 54. In FIG. 1, the control devices 56 are illustrated as a foot-operable control device 56' a hand-operable control device 56". It should be appreciated that control device 56' may be referred to herein as footswitch 56' and control device 56" may be referred to herein as handswitch 56". Additionally, these control devices 56 may be referred to in combination as "control devices 56', 56"".

In FIG. 1, the surgical handpieces 12 are physically coupled to the surgical console 54 at handpiece connection ports 58 and the control devices 56 are wirelessly coupled to the surgical console 54 at control connection ports 60. As shown, the surgical handpieces 12 are physically coupled to the handpiece connection ports 58 of the surgical console 54 using cables 26 (illustrated as cables 26', 26", 26"). Furthermore, the control devices 56 are wirelessly coupled to the surgical console 54 via dongles 62, which are physically coupled to the surgical console 54 at control connection ports 60. As such, the control devices 56 are able to remotely control the surgical handpieces 12. In other instances, the surgical handpieces 12 may be wirelessly coupled to the surgical console 54 in a manner similar to the control devices 56 in FIG. 1. In still other instances, the control devices 56 may be physically coupled to the surgical console 54 in a manner similar to the surgical handpieces 12 in FIG. 1.

The surgical console 54 may be of any suitable shape and size and may include components not shown in FIG. 1 or described herein. For example, the surgical console 54 may include any number of connection ports 58, 60. Additionally, the connection ports 58, 60 may be positioned on any suitable portion of the surgical console 54. Alternatively, the surgical console 54 may omit connection ports 58, 60 in instances where the surgical handpieces 12 and/or the control devices 56 may be wirelessly coupled to the surgical console 54.

In another example, the surgical console 54 may include visible light indicators around connection ports 58, 60 of the surgical console 54, which may be like those described in PCT Patent App. No. PCT/US18/29914, filed on Apr. 27, 2018, entitled, "System And Method For Indicating Mapping Of Console-Based Surgical Systems," the disclosure of which is hereby incorporated by reference in its entirety. Such an instance is shown in FIG. 1, where visible light emitted by the visible light indicators is represented using lines radiating from connection ports 58, 60. In such an instance, the visual indicators may be configured to emit visible light based on which control devices 56 control which surgical handpieces 12 (referred to herein as a "mapping configuration" and further described below). The visual indicators may also be configured to emit visible light based on successful connection of the surgical handpieces 12, dongles 62, and/or control devices 56. In yet another example, the surgical console 54 may include displays for displaying information from the surgical handpieces 12.

Additionally, the surgical console 54 may be stationary or mobile. The surgical console 54 may be any other device, such as a robotic manipulator, configured to enable control devices 56 to control surgical handpieces 12 coupled thereto. The surgical console 54 may be one of a variety of surgical consoles 102. For example, the surgical console 54 may be configured to provide capabilities for ultrasonic aspiration, suction, irrigation, RF ablation or lesioning, drilling, sawing, cutting, milling, imaging, and the like.

The control devices 56 may be foot-operable control devices (referred to herein as "footswitches") or hand-operable control devices (referred to herein as "hand-switches"). For example, in FIG. 1, the control devices 56 are illustrated using the footswitch 56' and the handswitch 56", respectively. The control devices 56 may include various different configurations to enable an operator to remotely control the surgical handpiece 12. The control devices 56 may include one or more sensors, such as Hall Effect sensors, magnetic sensors, load cells, pressure sensors, image sensors, inclinometers, or other sensors suitable for generating signals in response to a depression of a footswitch or handswitch.

In other examples, the control devices 56 may include voice-actuated control, knee-operated control, gesture-control, augmented/mixed reality control, or other types of control that may be actuated by an operator of the surgical system 10 and may be suitable for controlling a surgical handpiece 12. In such examples, the control devices 56 may include one or more sensors, such as Hall Effect sensors, magnetic sensors, load cells, pressure sensors, image sensors, inclinometers, or other sensors suitable for generating signals in response to an action of an operator of the control devices 56.

In still other examples, the control devices 56 may include a mobile computing device. Such mobile computing devices may include cellular phones, smart phones, laptops, tablets, wearable remote devices, or any other mobile computing device that is suitable for controlling a surgical handpiece 12. For example, the control device 56 may be a tablet customized for surgical applications and including a touchscreen. In such an example, an operator of the tablet may operate a surgical handpiece 12 by touching portions of the touchscreen and selecting commands for the surgical handpiece 12.

Additionally, control devices 56 may be coupled to light emitters 64, which are configured to emit visible light 66. In the instance of FIG. 1, the light emitters 64 are illustrated as light emitters 64', 64" and the visible light 66 is illustrated as visible light 66', 66". It should be noted that the light emitters 64 are similar to the light emitters 14 and any above description of the light emitters 14 also applies to the light emitters 64. For example, the light emitters 64 may be any suitable light emitter, such as at least one RGB LED.

It should be noted that the surgical system 10 may include any suitable number of control devices 56 for controlling the surgical handpieces 12 and each control device 56 may include any suitable number of light emitters 64. In the instance of FIG. 1, two control devices 56', 56" control the three surgical handpieces 12', 12", 12'''. As previously stated, the surgical system 10 may include any suitable number of surgical handpieces 12. Similarly, the surgical system 10 may include any suitable number of surgical handpieces 12 regardless of the number of surgical handpieces 12. For example, the surgical system 10 may include a fewer or greater number of control devices 56 than surgical handpieces 12. For example, the surgical system 10 in FIG. 1 includes three control devices 56 for controlling three surgical handpieces 12. Additionally, each control device 56 may include more than one light emitter 64.

Figure 4:
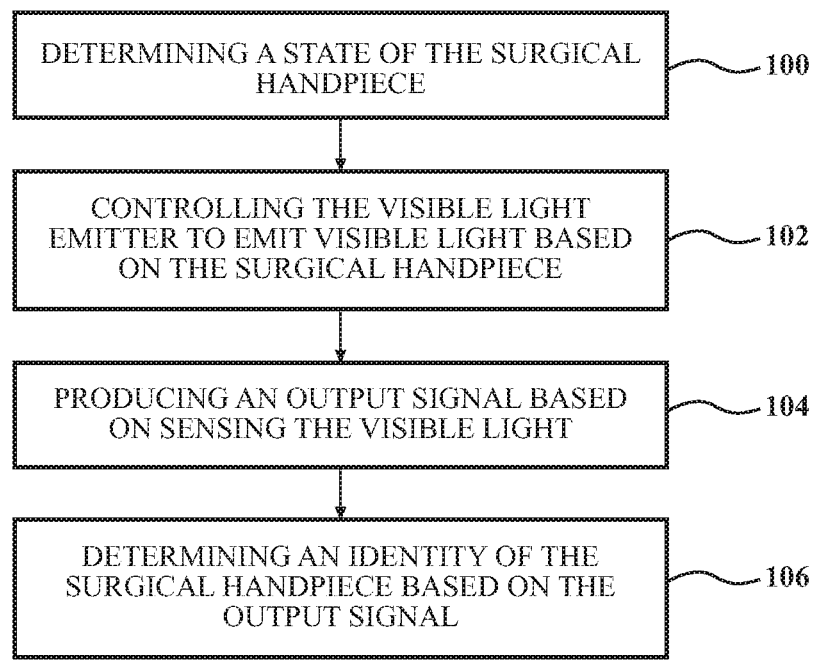
FIG. 4 is a flowchart of a method of operating the surgical system.

Referring now to FIG. 4, a method of operating the surgical system 10 with the above-stated components is shown. As shown, the method includes a step 100 of determining a state of the surgical handpieces 12, a step 102 of controlling the light emitters 14 to emit the visible light 20 based on the state of the surgical handpieces 12, a step 104 of producing the output signal based on sensing the visible light 20 emitted by the light emitters 14, and a step 106 of determining an identity of the surgical handpieces 12 based on the output signal.

The step 100 of determining the state of the surgical handpieces 12 may include a step (not shown) of determining at least one of an error condition of the surgical handpieces 12, an operational parameter of the surgical handpieces 12, an amount of power available to the surgical handpieces 12, a location of the surgical handpieces 12, a connection status of the surgical handpieces 12, an "in-use" status of the surgical handpieces 12, a mapping configuration of the surgical handpieces 12, and a mapping status of the surgical handpieces of the surgical handpieces 12. This step 100 may be executed by the controller 16.

In some instances, the controller 16 may be further configured to determine the state of the surgical handpiece 12 during step 100 based on a sensed reading produced by a sensor of the surgical system 10. In some instances, the surgical handpiece 12' includes the sensor. For example, referring to FIGS. 5A-5C, the sensor (not shown in FIGS. 5A-5C) may be disposed within the housing 24' of the surgical handpiece 12' and may be configured to produce a sensed reading of the surgical handpiece 12'. In an instance where the controller 16 is disposed within the surgical handpiece 12', the sensor and the light emitters 14' may be coupled to the controller 16 via a CAN communication network (not shown in FIGS. 5A-5C). As such, the controller 16 may quickly and efficiently receive the sensed reading from the sensor and control the light emitters 14'. Of course, any surgical handpiece 12 may similarly include the sensor. In other instances where the surgical system 10 includes the sensor, the sensor may be located outside the surgical handpiece 12, such as in an operating room including the surgical system 10. Additionally, any other component of the surgical system 10, such as the surgical console 54 may include the sensor.

The controller 16 may determine the state of the surgical handpieces 12 during step 100 by determining the error condition and/or the operational parameter of the surgical handpieces 12. For example, in an instance where the surgical handpiece 12 is a cutting tool, the surgical handpiece 12 may determine the error condition by determining that a short-circuit fault has occurred in the cutting tool, causing the motor of the cutting tool (such as the motor 99 shown in FIG. 5B) to be inoperable. Furthermore, in such an instance, the controller 16 may determine the operational parameter of the surgical handpiece 12 by determining a torque of the cutting tool, a speed of the cutting tool, a power consumed by the cutting tool, a frequency of the cutting tool vibration, a stall condition of the power tool, or combinations thereof. In instances where the surgical handpieces 12 include the above-described sensor, the sensor may be configured to sense error conditions and operational parameters of the surgical handpiece 12 and to produce a sensed reading accordingly.

In one instance where the surgical handpiece 12 is a cutting tool, the controller 16 may compare a speed of the cutting tool to a desired speed of the cutting tool based on a torque map. The controller 16 may determine a torque of the cutting tool based on a sensed current of a motor of the cutting tool and a torque constant. The motor of the cutting tool may be motor 99 shown in FIG. 5B. The motor may also be the handpiece motor described in U.S. Patent Application No. 2017/0172583 A1, entitled "Surgical Tool Assembly Including a Console, Plural Surgical Tools and a Footswitch, Wherein the Console is Able to Custom Map the Footswitch to each Surgical Tool," the disclosure of which is hereby incorporated by reference in its entirety. The controller 16 may also determine the speed of the cutting tool based on a back EMF waveform of the motor. Then, based on the torque of the cutting tool and the speed of the cutting tool, the controller 16 may determine a power consumed by the cutting tool using the torque map. The torque map may also provide a desired power consumed by the cutting tool and a desired torque and a desired speed of the cutting tool at the desired power consumed. The controller 16 may then compare the speed of the cutting tool to the desired speed of the cutting tool. In some instances, the desired power consumed by the cutting tool is a maximum power rating of the cutting tool.

In another instance where the surgical handpiece 12 is a cutting tool, the controller 16 may determine whether the cutting tool has reached a stall condition. A stall condition occurs when the cutting tool is unable to provide a torque capable of overcoming a load applied to the cutting tool and the cutting tool stops rotating. A stall condition may occur while the cutting tool is in use (i.e. after the cutting tool has begun rotating) or prior to the cutting tool beginning to rotate. The controller 16 may determine that a stall condition has been reached using a variety of methods. For example, the controller 16 may sense a non-zero user input (e.g. a user is activating the cutting tool), while also sensing that the cutting tool is not rotating based on a sensed speed of the cutting tool. In another example, the controller 16 may sense that a current is drawn by a motor of the cutting tool, but that the cutting tool is not rotating based on a sensed speed of the cutting tool.

The controller 16 may determine the state of the surgical handpieces 12 during step 100 based on an amount of power available to the surgical handpieces 12. For example, in an instance where multiple surgical handpieces 12 are coupled to the surgical console 54, the surgical console 54 distributes power across multiple surgical handpieces 12. As such, the controller 16 may determine an amount of power available to each of the surgical handpieces 12. In a more specific instance, the surgical console 54 may allocate the amount of power based on a type of the surgical handpiece 12. For example, if the surgical handpiece 12 coupled to the surgical console 54 may be one of a variety of drills, such as a high-powered tapered drill or a high-speed pencil-grip drill, the controller 16 may allocate a different amount of power to the drill based on a power rating of the drill. In such an example, the controller 16 may determine that an amount of power provided by the surgical console 54 is insufficient for powering one or more of the surgical handpieces 12.

The controller 16 may determine the state of the surgical handpieces 12 during step 100 by determining the location of the surgical handpieces 12. For example, the controller 16 may determine the location of the surgical handpieces 12 based on markers attached to the surgical handpiece 12. In another example where the surgical system 10 is operated in a bounded surgical site, the controller 16 may determine the position of the surgical handpieces 12 relative to a boundary of the surgical site. In yet another example, the controller 16 may determine the position of the surgical handpieces 12 relative to another component of the surgical system 10, such as another surgical handpiece 12. In instances where the above-stated sensor is located outside the surgical handpiece 12 (e.g., as a component of a surgical navigation system), the sensor may be configured sense marker located on the surgical handpieces 12 to determine the location of the surgical handpieces 12. In instances where the surgical handpieces 12 include the sensor, the sensor of the surgical handpieces 12 may be configured to sense the position of the surgical handpieces 12 relative to the boundary of the surgical site or relative to another surgical handpiece 12 and to produce a sensed reading accordingly.

The controller 16 may determine the state of the surgical handpieces 12 during step 100 by determining the connection status of the surgical handpieces 12. For example, in the instance of FIG. 1, the surgical console 54 is physically coupled to the surgical handpieces 12 and wirelessly coupled to the control devices 56. In such an instance, the connection status may include a status of the physical coupling of the surgical handpieces 12 and the surgical console 54 or a status of the wireless coupling of the control devices 56 and the surgical console 54. For instance, the controller 16 may determine that a surgical handpiece 12 or a control device 56 is disconnected from the surgical console 54 or connected improperly. The surgical handpieces 12, the control devices 56, the cables 26, the dongles 62, or the surgical console 54 may include the above-stated sensor and the sensor may be configured to sense the status of the coupling of the surgical handpieces 12 or the status of the coupling of the control devices 56 and to produce a sensed reading accordingly.

The controller 16 may determine the state of the surgical handpieces 12 during step 100 by determining the "in-use" status of the surgical handpieces 12. The "in-use" status of a surgical handpiece 12 is based on whether an operator of the surgical system 10 is using the surgical handpiece 12. For example, to determine the "in-use" status of a surgical handpiece 12, the controller 16 may sense whether the operator has depressed a trigger of the surgical handpiece 12.

Figure 3A:
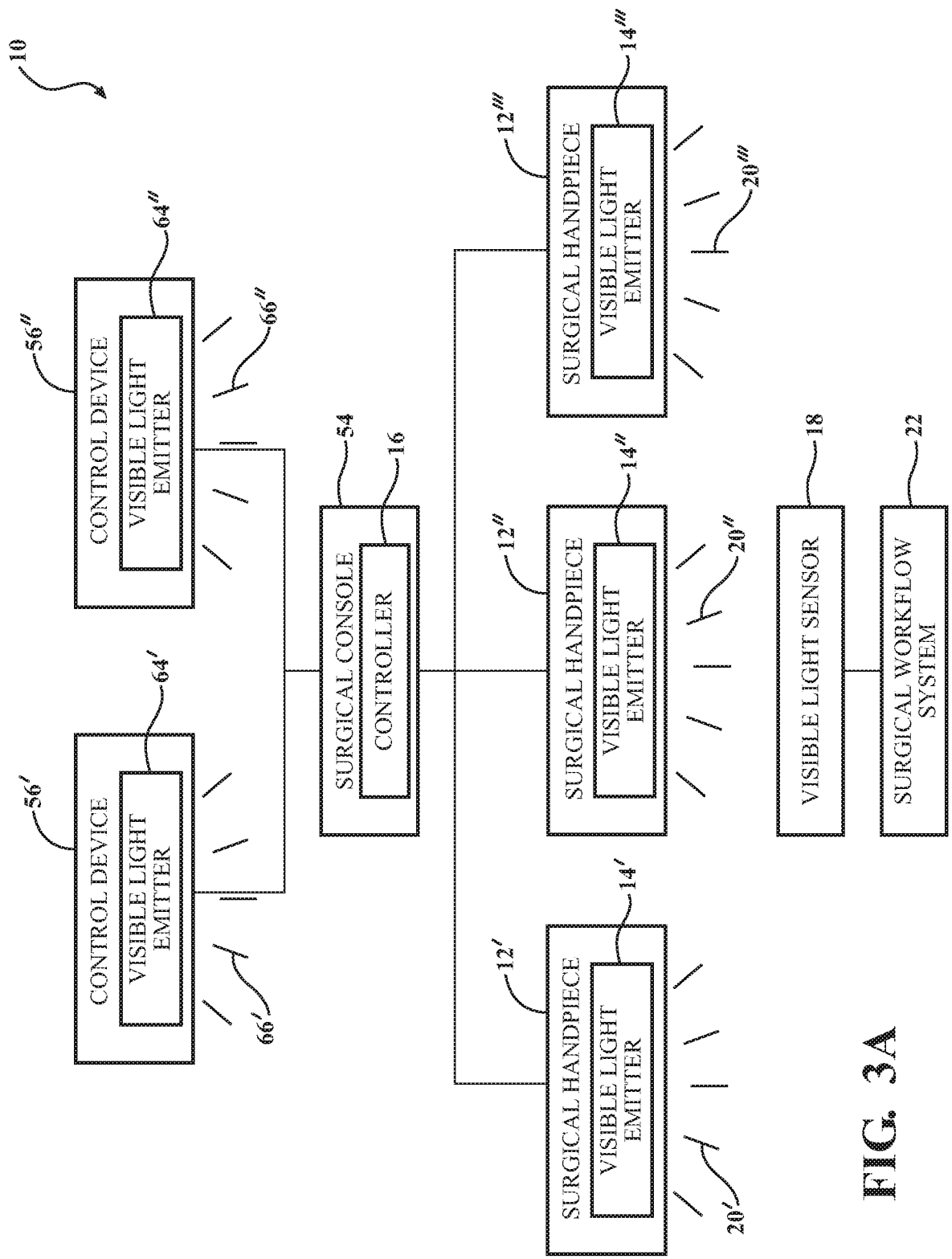
FIG. 3A is a schematic view of the instance of the surgical system in FIG. 1, wherein a surgical console comprises the controller of the surgical system.

The controller 16 may determine the state of the surgical handpieces 12 during step 100 by determining the mapping configuration of the surgical handpieces 12. A mapping configuration details which control devices 56 control which surgical handpieces 12. For example, to illustrate an example mapping configuration, FIG. 3A provides a schematic diagram of the instance of the surgical system 10 in FIG. 1. As shown in FIG. 3A, the surgical system 10 includes the three surgical handpieces 12', 12", 12''' and two control devices 56', 56". In an example instance of FIG. 3A, the footswitch 56' may be configured to control surgical handpiece 12' and the handswitch 56" may be configured to control surgical handpiece 12". In such an instance, the mapping configuration determined by controller 16 would detail the above configuration.

It should be noted that, if a control device 56 may be configured to control a surgical handpiece 12, the control device 56 may be referred to herein as being "mapped to" the surgical handpiece 12. Similarly, if a surgical handpiece 12 may be controlled by a control device 56, the surgical handpiece 12 may be referred to herein as being "mapped to" the control device 56.

The controller 16 may determine the mapping configuration using a variety of methods. In some instances, an operator of the surgical system 10 may use a touchscreen of the surgical console 54 to enter the mapping configuration. In such an instance, the operator may associate a specific handpiece connection port 150 with a specific control connection port 160 using the touchscreen of the surgical console 54. As such, the operator may specify that a control device 56 coupled to the specific control connection port 160 is mapped to a surgical handpiece 12 coupled to the specific handpiece connection port 150. As such, the controller 16 may receive the mapping configuration from the operator. In another instance, the controller 16 may automatically map a surgical handpiece 12 coupled to a handpiece connection port 150 to a control device 56 coupled to a control connection port 160 according to a default mapping configuration.

The controller 16 may determine the state of the surgical handpieces 12 during step 100 by determining the mapping status of the surgical handpieces 12. The mapping status of a surgical handpiece 12 is based on whether the surgical handpiece 12 may be controlled by a control device 56 according to a mapping configuration. For example, in an instance of FIG. 1 where surgical handpiece 12' is coupled to a handpiece connection port 58, but has not been mapped to either control devices 56', 56", the mapping status of the surgical handpiece 12' would reflect that surgical handpiece 12' is "unmapped". Conversely, in an instance of FIG. 1 where surgical handpiece 12" is coupled to a handpiece connection port 58 and has been mapped to a control device 56', 56", the mapping status of the surgical handpiece 12" would reflect that surgical handpiece 12" is "mapped".

The controller 16 may determine the mapping status of the surgical handpieces 12 using a variety of methods. For example, the controller 16 may determine that a surgical handpiece 12 is connected to the surgical console 54 using an above-described method of determining the connection status of the surgical handpiece 12 and may, by default, set the mapping status of the surgical handpiece 12 connected to a handpiece connection port 58 to "unmapped". The controller 16 may then set the mapping status of the surgical handpiece 12 to "mapped" after the controller 16 determines that the surgical handpiece 12 is mapped to a control device 56 using an above-described method of determining the mapping configuration of the surgical handpieces 12.

Figure 3B:
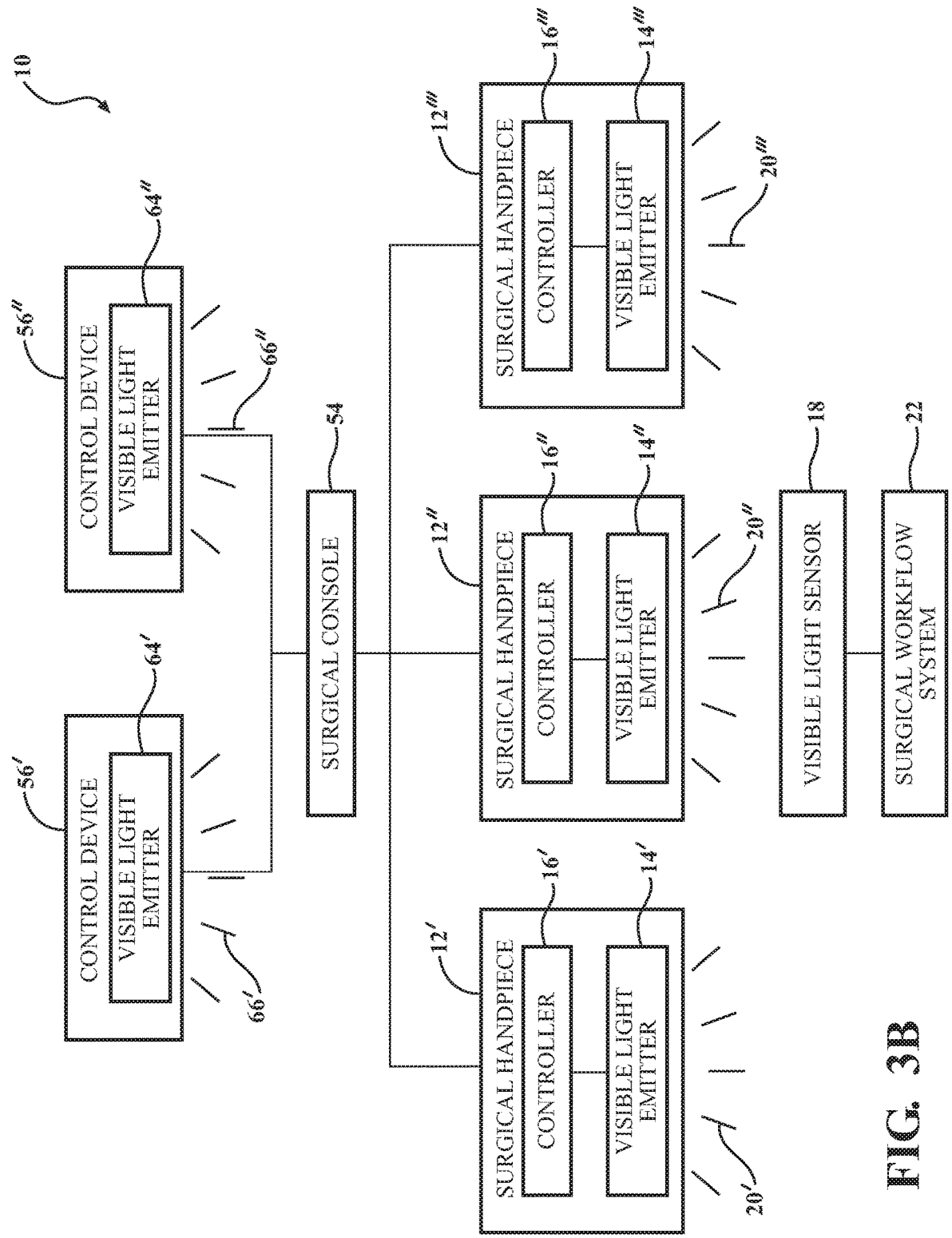
FIG. 3B is a schematic view of an instance of the surgical system comprising the plurality of surgical handpieces, the controller, the plurality of control devices, the light sensor, and the second surgical system, wherein the plurality of handheld surgical instruments comprises the controller of the surgical system.

It should be appreciated that the controller 16 may determine the state of the surgical handpieces 12 during step 100 using a variety of methods based on a location of the controller 16. For example, in FIG. 3A, the surgical console 54 includes the controller 16 in accordance with the "surgical console controller example" of FIG. 2A. In FIG. 3B, the surgical handpieces 12', 12", 12''' include the controller 16 as controller 16', 16", 16''', in accordance with the "surgical handpiece controller example". As such, while the controller 16 in FIG. 3A may determine the error condition, the operational parameter, the amount of power available, the connection status, the "in-use" status, the mapping configuration, and/or the mapping status of the surgical handpieces 12', 12", 12''', the controllers 16', 16", 16''' in FIG. 3B may determine the error condition, the operational parameter, the amount of power available, the connection status, the "in-use" status, the mapping configuration, and/or the mapping status of the surgical handpiece 12', 12", 12''' they are located within.

To illustrate how the controller 16 determines the state of the surgical handpieces 12 using a variety of methods based on a location of the controller 16, an instance where the controller 16 is located in the surgical console 54 (e.g., in FIG. 3A) and determines the mapping configuration of the surgical handpieces 12 is compared to an instance where the controller 16 is located in the surgical handpieces 12 (e.g., in FIG. 3B) and determines the mapping configuration of the surgical handpieces 12. The controller 16 in FIG. 3A may determine the mapping configuration of all surgical handpieces 12', 12", 12''', while the controllers 16', 16", 16''' in FIG. 3B may determine the mapping configuration of the surgical handpiece 12', 12", 12''' they are located within. For instance, the controller 16 in FIG. 3A may determine the mapping configuration of all surgical handpieces 12', 12", 12''' after an operator enters the mapping configuration into the surgical console 54 using a touchscreen of the surgical console 54. In contrast, the controllers 16', 16", 16''' in FIG. 3B may determine the mapping configuration of a surgical handpiece 12', 12", 12''' after an operator enters the mapping configuration into the surgical console 54 using the respective surgical handpiece 12', 12", 12''' (e.g., by simultaneously depressing a footswitch and a trigger on a surgical handpiece), after an operator enters the mapping configuration directly into the surgical handpieces 12', 12", 12''' (e.g., by using a button on a surgical handpiece), and/or by receiving the mapping configuration for the surgical handpiece 12', 12", 12''' from a controller in the surgical console 54.

Referring back to FIG. 4, the method includes the step 102 of controlling the light emitters 14 to emit the visible light 20 based on the state of the surgical handpieces 12. This step 102 may be executed by the controller 16. In some instances, the controller 16 may be configured to control the light emitter 14 by controlling a light color of the visible light 20 emitted by the light emitter 14. For example, in an instance where the light emitter 14 is at least one RGB LED, the controller 16 may be configured to control the light color of the visible light 20 emitted by the at least one RGB LED to be red, green, blue, or combinations thereof. In such instances, the light emitter 14 may be configured to control the light color of the visible light 20 emitted based on a wavelength of the visible light 20. For instance, the light emitter 14 may be configured to emit visible light 20 at a wavelength of 460 nm (corresponding to a blue light range of visible light).

Additionally, the controller 16 may be further configured to control the light emitter 14 during step 102 by controlling a light effect of the visible light 20 emitted by the light emitter 14. For example, the controller 16 may control the light effect of the visible light emitted by the light emitter 14 by controlling a light pattern and/or a light frequency of the visible light emitted by the light emitter 14.

For example, the controller 16 may be configured to control the light pattern of the visible light 20 emitted by the light emitter 14 by controlling the light emitter 14 such that the visible light 20 is emitted using a repeated pattern of pulses. In one such instance, the controller 16 may control the light emitter 14 to emit the visible light 20 with respect to a repeating period of "on" and "off phases", wherein the light emitter 14 emits the visible light 20 during the "on phase" and does not emit the visible light 20 during the "off phase". For example, during a 1.5 second period of "on" and "off phases", the light emitter 14 may emit the visible light 20 for 0.5 seconds during an "on phase", stop emitting the visible light 20 for 0.5 seconds during an "off phase", emit the visible light 20 for 0.25 seconds during an "on phase", and stop emitting the visible light 20 for 0.25 seconds during an "off phase". Of course, the controller 16 may control the light emitter 14 to repeatedly emit the visible light 20 using any suitable light pattern.

In another example, the controller 16 may be configured to control the light frequency of the visible light 20 emitted by the light emitter 14. For example, in some instances, the controller 16 may be configured to control the light frequency of the visible light 20 to be any light frequency greater than a predetermined frequency, such as 30 Hz. In some instances, this predetermined frequency may be based a flicker fusion frequency. The flicker fusion frequency is defined as a light frequency at which an intermittent light stimulus appears to be completely steady to an average human observer. As such, by controlling the light emitters 14 to emit the visible light 20 at light frequencies greater than the flicker fusion frequency, the intermittent nature of the visible light 20 is imperceptible to operators of the surgical system 10 and detectable only by components of the surgical system 10 (these components will be further discussed below). In an example instance, the flicker fusion frequency may be determined to be 60 Hz and the controller 16 may be configured to control the light emitter 14 such that the visible light 20 is emitted at a light frequency of 75 Hz.

Of course, the controller 16 may control one or more of the light color and the light effect of the visible light 20 emitted by the light emitter 14. In one such instance, the controller 16 may control the light color, the light pattern, and/or the light frequency of the visible light 20 emitted by the light emitter 14. For example, the controller 16 may be configured to control the light emitter 14 to emit the visible light 20 with respect to a repeating 2 second period including a 1 second "on phase" followed by a 1 second "off phase", wherein the light emitter 14 emits the visible light 20 with a red light color and at a light frequency of 80 Hz during each "on phase". Furthermore, it should be noted that, in other instances, the controller 16 may also control a light brightness of the light emitter 14.

In one example of the controller 16 controlling the light emitters 14 based on the state of the surgical handpiece 12 during step 102, the controller 16 may control the light color and/or the light pattern of the visible light 20 based on the error condition of the surgical handpieces 12. As previously described, the controller 16 may determine that a short-circuit fault has occurred in the surgical handpiece 12 and is therefore inoperable. In such an instance, the controller 16 may control the light emitter 14 of the surgical handpiece 12 to emit the visible light 20 with respect to a repeating 2 second period including a 1 second "on phase" followed by a 1 second "off phase", wherein the light emitter 14 emits the visible light 20 with a red light color during each "on phase".

In another example, the controller 16 may control the light color of the light emitters 14 based on the state of the surgical handpieces 12 by controlling the light color of the visible light 20 based on the operational parameter of the surgical handpieces 12. As previously described, in an instance where the surgical handpiece 12 is a cutting tool, the controller 16 may determine a speed of the cutting tool and control the light emitter 14 accordingly. In one such instance, the controller 16 may determine whether the speed of the cutting tool is too high or too low and control the light emitter 14 to emit the visible light 20 with a yellow light color accordingly. In some instances, if the speed of the cutting tool is within a correct range, the controller 16 may control the light emitter 14 to emit the visible light 20 with a green light color. In further instances, the controller 16 may control the light emitter 14 to emit the visible light 20 with a first light color, which corresponds to a first wavelength, when the speed of the cutting tool is within at a desired speed and a second light color, which corresponds to a second wavelength, when the speed of the cutting tool is too high or too low. In such instances, if the speed of the cutting tool is between the desired speed and a speed that is too high or too low, the controller 16 may control the light emitter 14 to emit the visible light 20 with a light color between the first and second light colors, which corresponds to a wavelength between the first and second wavelength.

In a more specific example where the controller 16 may control the light color of the light emitters 14 based on the operational parameter of the surgical handpieces 12, the controller 16 may control the light emitters 14 by controlling the light color of the visible light 20 based on comparing a sensed speed to a desired speed of a cutting tool (in an instance where a surgical handpiece 12 is a cutting tool). As previously stated, the controller 16 may, during step 100, compare a sensed speed to a desired speed of the cutting tool based on a torque map. The desired speed of the cutting tool may be chosen to based on a maximum power of the cutting tool. As such, the controller 16 may control the light emitter 14 of the surgical handpiece 12 to emit the visible light 20 with a green light color when the sensed speed is equivalent to the desired speed. Further, the controller 16 may control the light emitter 14 of the surgical handpiece 12 to emit the visible light 20 with a green-yellow light color when the sensed speed when the sensed speed is not equivalent to the desired speed, the green-yellow light color increasing in yellow hue as a magnitude of a difference between the desired speed and the sensed speed increases.

In another specific example where the controller 16 may control the light color of the light emitters 14 based on the operational parameter of the surgical handpieces 12, the controller 16 may control the light emitters 14 by controlling the light color of the visible light 20 based on a stall condition of a cutting tool (in an instance where a surgical handpiece 12 is a cutting tool). As previously stated, the controller 16 may determine with the cutting tool has reached a stall condition, wherein the cutting tool is unable to provide a torque capable of overcoming a load applied to the cutting tool and the cutting tool stops rotating. As such, the controller 16 may control the light emitter 14 of the surgical handpiece 12 to emit the visible light 20 with a red light color in the event that a stall condition has been reached.

In another example, the controller 16 may control the light emitters 14 based on the state of the surgical handpieces 12 during step 102 by controlling the light color of the visible light 20 based on an amount of power available to the surgical handpieces 12. As previously stated, the controller 16 may determine the amount of power available to a surgical handpiece 12 from the surgical console 54. In one such instance where multiple surgical handpieces 12 are coupled to the surgical console 54, the controller 16 may determine an amount of power available to each of the surgical handpieces 12 from the surgical console 54. As such, the controller 16 may control the light emitter 14 of the surgical handpiece 12 to emit the visible light 20 with a green light color when the surgical handpiece 12 is not "in-use", but a sufficient amount of power is available to the surgical handpiece 12. The controller 16 may also control the light emitter 14 of the surgical handpiece 12 to emit the visible light 20 with a red light color when the surgical handpiece 12 is not "in-use" and sufficient amount of power is not available to the surgical handpiece 12.

In yet another example, the controller 16 may control the light emitters 14 based on the state of the surgical handpieces 12 during step 102 by controlling the light color of the visible light 20 based on a location of a corresponding surgical handpiece 12. As previously described, the controller 16 may determine the position of the surgical handpiece 12 relative to a boundary of the surgical site and to another component of the surgical system 10. As such, the controller 16 may control the light emitter 14 of the surgical handpiece 12 to emit the visible light 20 with a yellow light color when the surgical handpiece 12 is near a boundary of the surgical site or near an incompatible component of the surgical system 10.

In still another example, in instances where the surgical handpieces 20 include a power source (e.g. a battery), the controller 16 may control the light emitters 14 based on the state of the surgical handpieces 12 by controlling the light color of the visible light 20 based on the connection status of the surgical handpieces 12. As previously described, the controller 16 may determine the connection status of the surgical handpiece 12 by determining that the surgical handpiece 12 is disconnected from the surgical console 54. For example, in instances where the surgical handpiece 12 is battery-powered, the controller 16 may determine that the surgical handpiece 12 is not physically coupled or wirelessly coupled to the surgical console 54. In such instances, the controller 16 may control the light emitter 14 of the surgical handpiece 12 to emit the visible light 20 with respect to a repeating 1 second period including a 0.5 second "on phase" followed by a 0.5 second "off phase".

In still yet another example, the controller 16 may control the light emitters 14 based on the state of the surgical handpieces 12 during step 102 by controlling the light pattern of the visible light 20 based on the "in-use" status of the surgical handpieces 12. As previously described, the controller 16 may determine the "in-use" status of the surgical handpiece 12 based on whether an operator of the surgical system 10 is using the surgical handpiece 12. In such an instance, the controller 16 may control the light emitter 14 of the surgical handpiece 12 to emit the visible light 20 with respect to a repeating 2 second period including a 1 second "on phase" followed by a 1 second "off phase", wherein the light emitter 14 emits the visible light 20 with a green light color during each "on phase".

The controller 16 may also control the light emitters 14 to emit the visible light 20 based on the mapping configuration. The schematic view of FIG. 3A further illustrates the step 102 of controlling the light emitter 14 based on the mapping configuration. As shown, the surgical system 10 includes the surgical handpieces 12', 12", 12' coupled to the light emitters 14', 14", 14''' and the control devices 56', 56" coupled to light emitters 64', 64". In one instance, the controller 16 controls the light emitters 14', 14", 14' based on the mapping configuration by controlling the light color of the visible light 20', 20", 20''' to correspond with a light color of the visible light 66', 66" emitted by the light emitters 64', 64".

For example, in a specific instance of FIG. 3A, the footswitch 56' controls the surgical handpiece 12' and the handswitch 56" controls the surgical handpiece 12" according to the mapping configuration. In such an instance, the visible light 66' emitted by the light emitter 64' has an orange light color and the visible light 66" emitted by the light emitter 64" has a blue light color. As such, the controller 16 controls the light emitter 14' to emit the visible light 20' with a corresponding orange light color to indicate that the footswitch 56' is mapped to, and therefore controls, the surgical handpiece 12'. Similarly, the controller 16 controls the light emitter 14" to emit the visible light 20" with a corresponding blue light color to indicate that the handswitch 56" is mapped to, and therefore controls, the surgical handpiece 12".

As another example, in a specific instance of FIG. 3A, the surgical handpiece 12' is mapped to either control device 56', 56" according to the mapping configuration. In such an instance, the visible light 66', 66" emitted by the light emitters 64', 64" have an orange and blue light color, respectively. As such, the controller 16 controls the light emitter 14' to emit the visible light 20' with a corresponding orange and blue light color to indicate that the control devices 56', 56" are both mapped to the surgical handpiece 12'. In such an instance, the controller 16 may control the light emitter 14' to simultaneously or sequentially emit the visible light 20' with the orange and blue light color.

The controller 16 may also control the light emitters 14 based on the state of the surgical handpieces 12 during step 102 by controlling the light color and the light pattern of the visible light 20 based on the mapping status of the surgical handpieces 12. As previously described, the controller 16 may determine the mapping status of a surgical handpiece 12 based on determining whether the surgical handpiece 12 is connected to the surgical console 54 and based on determining whether the surgical handpiece 12 has been mapped to a control device 56 in a mapping configuration. In one such instance, the controller 16 may control the light emitter 14 of the surgical handpiece 12 to emit the visible light 20 with respect to a repeating 2 second period including a 1 second "on phase" followed by a 1 second "off phase", wherein the light emitter 14 emits the visible light 20 with a white light color during each "on phase" if the surgical handpiece 12 has a mapping status of "unmapped".

The controller 16 may also control the light emitters 14 to emit the visible light 20 based on an identity of the surgical handpieces 12. The schematic view of FIG. 3A further illustrates the step 102 of controlling the light emitter 14 based on the identity of the surgical handpieces 12. For example, in the instance of FIG. 3A, the controller 16 may control the light effect of the visible light 20', 20", 20''' emitted by the light emitters 14', 14", 14' based on the identity of the surgical handpieces 12', 12", 12'''. In one such instance, the controller 16 may predetermine a light frequency for each surgical handpiece 12', 12", 12'. As such, the controller may then control the light emitters 14', 14", 14'" to emit the visible light 20', 20", 20'" at the predetermined light frequencies. For example, the controller 16 may control the light emitters 14', 14", 14'" to emit the visible light 20', 20", 20' at a light frequency of 75 Hz, 100 Hz, and 125 Hz, respectively. Again, it should be noted that, these light frequencies, 75 Hz, 100 Hz, 125 Hz, may be chosen based on a flicker fusion frequency such that the intermittent nature of visible light 20', 20", 20'" is imperceptible to operators of the surgical system 10 and detectable only by components of the surgical system 10 (these components will be further discussed below).

It should be noted that the controller 16 may control the light emitters 14 based on one or more of the error condition, the operational parameter, the amount of power available, the connection status, the location, the "in-use" status, the mapping configuration, the mapping status, and the identity of the surgical handpieces 12. In one such instance, the controller 16 controls the light emitter 14 based on the mapping configuration and the identity of the surgical handpieces 12. For example, in an instance of FIG. 3A, the controller 16 may control the light emitter 14' to emit the visible light 20' with an orange light color and at a light frequency of 75 Hz based on the mapping configuration and the identity of the surgical handpiece 12', respectively. In another example, in an instance of FIG. 3A, the controller 16 may control the light emitter 14' to emit the visible light 20' with respect to a repeating 2 second period including a 1 second "on phase" followed by a 1 second "off phase", wherein the light emitter 14' emits the visible light 20' with a red light color based on the connection status and at a light frequency of 80 Hz during each "on phase" based on the identity of the surgical handpiece 12'.

Furthermore, it should be noted that in the instance of FIG. 3B, which is in accordance with the "surgical handpiece controller example", the controller 16', 16", 16'" control each of the light emitters 14', 14", 14'" based on the state of the surgical handpieces 12', 12", 12'", respectively. For example, the controller 16' may control the light emitter 14' to emit the visible light 20' with an orange light color and at a light frequency of 75 Hz based on the mapping configuration and the identity of the surgical handpiece 12', respectively. Similarly, the controller 16', 16", 16'" may control each of the light emitters 14', 14", 14'" based on at least one of the error condition, the operational parameter, the amount of power available the connection status, the location, the "in-use" status, and the mapping status of the surgical handpieces 12', 12", 12'", respectively.

Additionally, it should be noted that all above examples are not intended to limit the controller 16. For instance, in the above examples, the controller 16 controls the light color of the visible light 20 based on the mapping configuration of the surgical handpieces 12 and the light frequency of the visible light 20 based on the identity of the surgical handpieces 12. However, in other instances, the controller 16 may control the light frequency or the light pattern of the visible light 20 based on the mapping configuration of the surgical handpieces 12 and the light color or light pattern of the visible light 20 based on the identity of the surgical handpieces 12. Similarly, the controller 16 may control the light frequency or light pattern of the visible light 20 based on the error condition, the operational parameter, the amount of power available, the location, the connection status, the "in-use" status, and the mapping status of the surgical handpiece.

Referring back to FIG. 4, the method includes the step 104 of producing the output signal based on sensing the visible light 20 emitted by the light emitters 14. This step 104 may be executed by the light sensor 18. For example, in the instance of FIGS. 3A and 3B, the light sensor 18 senses the visible light 20', 20", 20'" emitted by the light emitters 14', 14", 14'" and produces the output signal based on the visible light 20', 20", 20'".

The light sensor 18 may sense the light color and the light effect of the visible light 20 and produce the output signal accordingly. For example, in an example instance of FIG. 3A or FIG. 3B, the light sensor 18 may sense that the light emitter 14' is emitting the visible light 20' with respect to a repeating 2 second period including a 1 second "on phase" followed by a 1 second "off phase", wherein the light emitter 14 emits the visible light 20 with an orange light color and at a light frequency of 75 Hz during each "on phase". Accordingly, the output signal produced by the light sensor 18 may indicate orange as the light color, the repeating 2 second period as the light pattern, and 75 Hz as the light frequency of the visible light 20'.

Additionally, the light sensor 18 may simultaneously sense the visible light 20', 20", 20'" emitted by light emitters 14', 14", 14'" and produce the output signal accordingly. For example, in an example instance of FIG. 3A or FIG. 3B, the light sensor 18 may sense that the light emitter 14' is emitting the visible light 20' with an orange light color and at a light frequency of 75 Hz, that the light emitter 14" is emitting visible light 20" with an orange and blue light color and at a light frequency of 100 Hz, and that the light emitter 14'" is simultaneously emitting visible light 20'" with a blue light color and at a light frequency of 125 Hz. The light sensor 18 may then produce the output signal accordingly.

Furthermore, in instances where the light sensor 18 is a digital camera or a video camera, the output signal may be a recording or a photo of the visible light 20. In such instances, the second surgical system 22 may determine the light color and/or light effect after receiving the output signal from the light sensor 18 with image processing.

Again referring back to FIG. 4, the method includes the step 106 of determining the identity of the surgical handpieces 12 based on the output signal. This step 106 may be executed by the second surgical system 22. Additionally, the second surgical system 22 may be further configured to determine the state of the surgical handpieces 12 based on the output signal. For example, the second surgical system 22 may determine the state and the identity of the surgical handpieces 12 based on receiving the light color and the light effect of the visible light 20 from the output signal. In one such instance, the second surgical system 22 may determine the state of the surgical handpieces 12 based on the light color and the light pattern of the surgical handpieces 12, the state of the surgical handpiece being at least one of the error condition, the operational parameter, the amount of power available, the connection status, the "in-use" status, the mapping configuration, and/or the mapping status of the surgical handpieces 12', 12", 12'". In such an instance, the second surgical system 22 may determine the identity of the surgical handpieces 12 based on the light frequency.

For example, in an instance of FIG. 3A or FIG. 3B where the light emitter 14' is emitting the visible light 20' with an orange light color and at a light frequency of 75 Hz, the second surgical system 22 may identify the surgical handpiece 12' based on the 75 Hz light frequency and may determine that the surgical handpiece 12' is mapped to footswitch 56' based on the orange light color. Similarly, in an instance where the light emitter 14' is emitting the visible light 20' with respect to a repeating 2 second period including a 1 second "on phase" followed by a 1 second "off phase", wherein the light emitter 14 emits the visible light 20 with a red light color and at a light frequency of 75 Hz during each "on phase", the second surgical system 22 may identify the surgical handpiece 12' based on the 75 Hz light frequency and determine that the surgical handpiece 12' (which includes a power source) is not physically coupled or wirelessly coupled to the surgical console 54 based on the red light color and the repeating 2 second period.

In another instance of FIG. 3A or FIG. 3B, the light emitter 14' emits the visible light 20' with an orange light color and at a light frequency of 75 Hz, the light emitter 14" emits visible light 20" with an orange and blue light color and at a light frequency of 100 Hz, and the light emitter 14''' emits the visible light 20''' with a blue light color and at a light frequency of 125 Hz. In such an instance, the second surgical system 22 may identify the surgical handpieces 12', 12", 12''' based on the respective light frequencies. The second surgical system 22 may also determine that the surgical handpiece 12' is mapped to footswitch 56' based on the orange light color, that the surgical handpiece 12" is mapped to the control devices 56', 56" based on the orange and blue light color, and that the surgical handpiece 12''' is mapped to the handswitch 56" based on the blue light color.

It should again be noted that all above examples are not intended to limit the controller 16. For instance, in the above examples of the second surgical system 22, the second surgical system 22 determines the state of the surgical handpieces 12 based on the light color and the light pattern of the surgical handpieces 12 and determines the identity of the surgical handpieces 12 based on the light frequency. However, in other instances of the second surgical system 22, the second surgical system 22 may determine the state of the surgical handpieces 12 or the identity of the surgical handpieces 12 in different ways based on how the controller 16 controls the light emitters 14 during the step 102 of controlling the light emitters 14. For example, in instances where the controller 16 controls the light frequency of the visible light 20 based on the mapping configuration, the second surgical system 22 may determine the mapping configuration based on the light frequency. As another example, in instances where the controller 16 determines the identity of the surgical handpieces 12 based on light color or light pattern, the second surgical system 22 may determine the identity of the surgical handpieces 12 based on light color or light pattern.

As previously stated, the light frequencies at which the light emitters 14 emit the visible light 20 may be chosen based on the flicker fusion frequency, allowing the intermittent nature of the visible light 20 to be imperceptible by operators of the surgical system 10. However, the light sensor 18 is configured to sense the light frequency of the visible light 20 above the flicker fusion frequency and to produce an output signal accordingly. Furthermore, the second surgical system 22 is able to determine the identity of the surgical handpieces 12 based on the output signal. As such, by controlling the light emitters 14 to emit the visible light 20 at a light frequency greater than the flicker fusion frequency, the controller 16 advantageously allows for transmission of information of the surgical handpieces 12 by the second surgical system 22 without distracting operators of the surgical system 10 with the flickering of visible light 20.

After determining the identity of the surgical handpieces 12 based on the output signal, the second surgical system 22 may be further configured to perform a variety of tasks. For example, as previously stated, the second surgical system 22 may be configured to determine, based on the identity of the surgical handpiece 12, a step (current, previous, or subsequent) of the surgical procedure, instructions for the step of the surgical procedure, whether the surgical handpiece 12 is acceptable for the step of the surgical procedure, warnings for the step of the surgical procedure, whether the surgical procedure requires additional surgical handpieces 12 or auxiliary equipment (operating room lighting, video and sound recording devices, suction devices, imaging devices, etc.), and/or whether the surgical handpiece 12 includes an attachment.

Additionally, the second surgical system 22 may perform additional tasks after determining the identity of the surgical handpieces 12 and after determining the state of the surgical handpieces 12 based on the output signal. For instance, after determining the identity and the state of a surgical handpiece 12, the second surgical system 22 links the determined state to the identified surgical handpiece 12. The second surgical system 22 may then provide the state of the identified surgical handpiece 12 to an operator of the surgical system 10.

It should be noted that, in some instances, the second surgical system 22 may omit a step of determining the state of the surgical handpieces 12 based on the output signal. For example, in some instances, an operator of the surgical system 10 may determine the state of the surgical handpieces 12 based on the visible light 20. For example, an operator of the surgical system 10 may determine whether a surgical handpiece 12 is mapped to a control device 56 by visually observing a light color of the visible light 20, 66 emitted by a light emitter 14 of the surgical handpiece 12 and a light emitter 64 of the control device 56, respectively. In one such instance where the light emitter 14 of a surgical handpiece 12 and a light emitter 64 of a control device 56 emit visible light 20, 66, respectively, using a blue light color, an operator of the surgical system 10 may observe the blue light color and determine that the surgical handpiece 12 is mapped to the control device 56. However, in instances where the second surgical system 22 may perform additional tasks based on determining the state of the surgical handpieces 12, the second surgical system 22 may be configured to determine the state of the surgical handpieces 12.

For example, after determining the identity and the state of a surgical handpiece 12, the second surgical system 22 may display a GUI on a screen in the operating room of the surgical system 10, the GUI providing a step of the surgical procedure, instructions, and/or warnings regarding the identified surgical handpiece 12 as well as at least one of the error condition, the operational parameter, the amount of power available, the connection status, the "in-use" status, the mapping configuration, and/or the mapping status of the identified surgical handpiece 12.

In another example, the second surgical system 22 may determine the identity and the mapping configuration of the surgical handpieces 12 and link the mapping configuration to the identity of the surgical handpieces 12. As such, the second surgical system 22 may perform an additional task of detecting changes in the mapping configuration of the surgical handpieces 12. For instance, at a first time, surgical handpiece 12' of FIG. 1A may be mapped to footswitch 56' and at a second time, surgical handpiece 12" may be mapped to footswitch 56'. By linking the mapping configuration of the surgical handpieces 12 to the identity of the surgical handpieces 12, the second surgical system 22 is able to identify if a different surgical handpiece 12 is mapped to a control device 56.

In yet another example, the second surgical system 22 may determine the identity and the mapping status of a surgical handpiece 12 and link the mapping status to the identity of the surgical handpieces 12. As such, the second surgical system 22 may perform an additional task of automatically mapping a control device 56 to an appropriate, "unmapped" surgical handpiece 12. For instance, the second surgical system 22 may determine that a surgical handpiece 12 is "unmapped" by determining the mapping status of the surgical handpiece 12. The second surgical system 22 may then determine the identity of the surgical handpiece 12 to determine whether the surgical handpiece 12 is a surgical handpiece 12 which may be appropriately mapped to a control device 56. This determination of whether a surgical handpiece 12 may be appropriately mapped may be based on any suitable factor, such as a type of the surgical handpiece 12, a type of the control devices 56, and/or a step of the surgical procedure. As such, by linking the mapping status and the identity, the second surgical system 22 may automatically map an appropriate, "unmapped" surgical handpiece 12 to a control device 56. The second surgical system 22 may then provide a new mapping configuration to the surgical console 54, reflecting the automatic mapping.

In still another example where the second surgical system 22 includes a surgical navigation system, the second surgical system 22 may determine the identity and the location of a surgical handpiece 12 based on the output signal and link the location to the identity of the surgical handpiece 12. As such, the second surgical system 22 may perform an additional task of calibrating the surgical navigation system. For instance, to calibrate the surgical navigation system, the second surgical system 22 may require an operator of the surgical system 10 to follow a calibration procedure, which may require the operator of the surgical system 10 to place a specific surgical handpiece 12 at certain known locations and to depress a trigger on the specific surgical handpiece after the specific surgical handpiece 12 has been placed accordingly. As such, by linking the location of the surgical handpiece 12 to the identity of the surgical handpieces 12, the second surgical system 22 is able to determine when the specific surgical handpiece 12 is placed accordingly.

It will be further appreciated that the terms "include," "includes," and "including" have the same meaning as the terms "comprise," "comprises," and "comprising."

Several instances have been discussed in the foregoing description. However, the instances discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. An autoclavable surgical handpiece comprising:
   a housing having a first end and a second end;
   a visible light emitter disposed within the housing;
   a controller disposed within the housing and coupled to the visible light emitter, the controller being configured to determine a state of the autoclavable surgical handpiece and to control the visible light emitter to emit visible light based on the state of the autoclavable surgical handpiece; and
   a potting material disposed between the visible light emitter and the first end of the housing, the potting material having a melting point above 120 degrees Celsius and being configured to thermally insulate the visible light emitter and to transmit visible light emitted by the visible light emitter therethrough.

2. The autoclavable surgical handpiece of claim 1, further comprising:
   a cable adjacent to the housing, the cable having an external surface; and
   a strain relief member coupled to the external surface of the cable and disposed adjacent to the first end of the housing, the strain relief member having a melting point above 120 degrees Celsius and being configured to seal the cable to the housing and to transmit visible light emitted by the visible light emitter therethrough.

3. The autoclavable surgical handpiece of claim 2, wherein the visible light emitter is disposed within the housing such that the visible light emitted by the visible light emitter is directed towards the strain relief member.

4. The autoclavable surgical handpiece of claim 2, wherein the strain relief member is transparent.

5. The autoclavable surgical handpiece of claim 2, wherein the potting material and the strain relief member are formed of the same material.

6. The autoclavable surgical handpiece of claim 2, wherein the potting material and the strain relief member are formed as a single member.

7. The autoclavable surgical handpiece of claim 1, wherein the potting material is transparent.

8. The autoclavable surgical handpiece of claim 1, wherein the controller is configured to control a light color of the visible light emitted by the visible light emitter.

9. The autoclavable surgical handpiece of claim 1, wherein the controller is configured to control a light effect of the visible light emitted by the visible light emitter.

10. The autoclavable surgical handpiece of claim 9, wherein the light effect comprises at least one of a light frequency and a light pattern.

11. The autoclavable surgical handpiece of claim 1, wherein the surgical handpiece comprises a sensor disposed within the housing and coupled to the controller, the sensor being configured to produce a sensed reading of the surgical handpiece and the controller being configured to determine the state based on the sensed reading.

12. The autoclavable surgical handpiece of claim 1, wherein the surgical handpiece comprises a CAN communication network, and at least one of the sensor and the visible light emitter are coupled to the controller via the CAN communication network.

13. The autoclavable surgical handpiece of claim 1, wherein the visible light emitter comprises at least one of an LED, an optical fiber, and combinations thereof.

* * * * *